US012588922B2

(12) United States Patent
Sholev et al.

(10) Patent No.: US 12,588,922 B2
(45) Date of Patent: Mar. 31, 2026

(54) STERILE BARRIERS AND SENSOR SETS FOR A MEDICAL DEVICE

(71) Applicant: Human Xtensions Ltd., Netanya (IL)

(72) Inventors: Mordehai Sholev, Moshav Amikam (IL); Liran Elihay, Kiryat Gat (IL); Oren Teiblum, Hod-HaSharon (IL); Itai Meshorer, Tel-Aviv (IL); Assaf Kaufman, Tal Shahar (IL); Tal Korman, Tel-Aviv (IL); Gil Vitenberg, RaAnana (IL); Eytan Mashiach, Zufim (IL)

(73) Assignee: HumanTouch Surgical Ltd, Netanya (IL)

( * ) Notice: Subject to any disclaimer, the term of this patent is extended or adjusted under 35 U.S.C. 154(b) by 609 days.

(21) Appl. No.: 17/622,725

(22) PCT Filed: Jun. 30, 2020

(86) PCT No.: PCT/IL2020/050728
§ 371 (c)(1),
(2) Date: Dec. 24, 2021

(87) PCT Pub. No.: WO2021/001822
PCT Pub. Date: Jan. 7, 2021

(65) Prior Publication Data
US 2022/0249111 A1 Aug. 11, 2022

Related U.S. Application Data

(60) Provisional application No. 62/868,940, filed on Jun. 30, 2019.

(51) Int. Cl.
*A61B 17/29* (2006.01)
*A61B 34/00* (2016.01)
(Continued)

(52) U.S. Cl.
CPC .......... *A61B 17/2909* (2013.01); *A61B 34/25* (2016.02); *A61B 46/10* (2016.02);
(Continued)

(58) Field of Classification Search
CPC ..................... A61B 34/25; A61B 2017/00017
See application file for complete search history.

(56) References Cited

U.S. PATENT DOCUMENTS

| | | | |
|---|---|---|---|
| 5,630,986 A | 5/1997 | Charlton et al. | |
| 10,052,157 B2 | 8/2018 | Frimer et al. | |

(Continued)

FOREIGN PATENT DOCUMENTS

| | | |
|---|---|---|
| CN | 101166465 | 4/2008 |
| CN | 103281983 | 9/2013 |

(Continued)

OTHER PUBLICATIONS

Notification of Office Action and Search Report Dated Feb. 3, 2024 From the National Intellectual Property Administration of the People's Republic of China Re. Application No. 202080053708.7 and Its Machine Translation Into English. (14 Pages).
(Continued)

*Primary Examiner* — Carl H Layno
*Assistant Examiner* — Maria Catherine Anthony

(57) ABSTRACT

Sterile barriers and sensor configurations for a medical device are described. The sterile barriers isolate internal components such as a battery pack or a sensor pack from the environment and the patient.

2 Claims, 22 Drawing Sheets

(51) Int. Cl.

| | | |
|---|---|---|
| *A61B 46/10* | (2016.01) | |
| *A61B 90/50* | (2016.01) | |
| *A61B 17/00* | (2006.01) | |
| *A61B 34/20* | (2016.01) | |
| *A61B 90/00* | (2016.01) | |

(52) U.S. Cl.
CPC .... *A61B 90/50* (2016.02); *A61B 2017/00207* (2013.01); *A61B 2017/00212* (2013.01); *A61B 2017/00389* (2013.01); *A61B 2017/00398* (2013.01); *A61B 2017/00424* (2013.01); *A61B 2017/00442* (2013.01); *A61B 2017/00734* (2013.01); *A61B 2034/2048* (2016.02); *A61B 2090/0813* (2016.02)

(56) References Cited

U.S. PATENT DOCUMENTS

| | | | |
|---|---|---|---|
| 2003/0032190 A1* | 2/2003 | Brown | G07F 11/54 |
| | | | 435/14 |
| 2005/0222587 A1 | 10/2005 | Jinno et al. | |
| 2009/0253961 A1 | 10/2009 | Le et al. | |
| 2016/0089154 A1 | 3/2016 | Chien et al. | |
| 2016/0184040 A1 | 6/2016 | Sholcv | |
| 2016/0310134 A1* | 10/2016 | Contini | A61B 17/0686 |
| 2017/0157361 A1* | 6/2017 | Barrish | A61B 17/00234 |
| 2018/0161110 A1 | 6/2018 | Overmyer et al. | |
| 2019/0021636 A1 | 1/2019 | Walter | |
| 2019/0069968 A1 | 3/2019 | Sholev | |
| 2019/0083017 A1 | 3/2019 | Walter | |
| 2019/0200987 A1* | 7/2019 | Shelton, IV | A61B 90/98 |

FOREIGN PATENT DOCUMENTS

| | | | | |
|---|---|---|---|---|
| CN | 104487007 A * | 4/2015 | | A61B 17/14 |
| CN | 106377315 | 2/2017 | | |
| CN | 108992103 | 12/2018 | | |
| EP | 1584300 | 10/2005 | | |
| JP | H06-304176 | 11/1994 | | |
| JP | 2016-533241 | 10/2016 | | |
| JP | 2019-503721 | 2/2019 | | |
| JP | 2019-509806 | 4/2019 | | |
| WO | WO 2014/033717 | 3/2014 | | |
| WO | WO-2014033717 A1 * | 3/2014 | | A61B 17/2909 |
| WO | WO 2015/029041 | 3/2015 | | |
| WO | WO 2016/157171 | 10/2016 | | |
| WO | WO 2017154007 | 9/2017 | | |
| WO | WO 2018/134830 | 7/2018 | | |
| WO | WO 2018/157135 | 8/2018 | | |
| WO | WO 2021/001822 | 1/2021 | | |

OTHER PUBLICATIONS

Notice of Reasons for Rejection Dated Mar. 5, 2024 From the Japan Patent Office Re. Application No. 2021-576518 and its Translation Into English. (8 Pages).

Supplementary European Search Report and the European Search Opinion Dated Mar. 1, 2024 From the European Patent Office Re. Application No. 20835138.7. (9 Pages).

International Search Report and the Written Opinion Dated Oct. 9, 2020 From the International Searching Authority Re. Application No. PCT/IL2020/050728. (12 Pages).

Decision on Rejection Dated May 1, 2024 From the State Intellectual Property Office of the People's Republic of China Re. Application No. 202080053708.7 and Its Machine Translation Into English. (12 Pages).

Examination Report Under Sections 12 & 13 of the Patents Act, 1970 and the Patents Rules, 2003 Dated Jan. 19, 2024 From the Government of India, Intellectual Property India, Patents, Designs, Trade Marks, Geographical Indications, The Patent Office Re. Application No. 202227002648. (7 pages).

English Summary of Decision on Rejection Dated May 1, 2024 From the State Intellectual Property Office of the People's Republic of China Re. Application No. 202080053708.7. (3 Pages).

English Summary Dated Oct. 23, 2023 Notification of Office Action Dated Oct. 13, 2023 From the National Intellectual Property Administration of the People's Republic of China Re. Application No. 202080053708.7. (4 Pages).

Machine Translation Dated Oct. 18, 2023 Notification of Office Action Dated Oct. 13, 2023 From the National Intellectual Property Administration of the People's Republic of China Re. Application No. 202080053708.7. (7 Pages).

Notification of Office Action and Search Report Dated Oct. 13, 2023 From the National Intellectual Property Administration of the People's Republic of China Re. Application No. 202080053708.7. (7 Pages).

International Preliminary Report on Patentability Dated Jan. 13, 2022 From the International Bureau of WIPO Re. Application No. PCT/IL2020/050728. (6 Pages).

English Summary Dated Feb. 27, 2024 of Notification of Office Action and Search Report Dated Feb. 3, 2024 From the National Intellectual Property Administration of the People's Republic of China Re. Application No. 202080053708.7. (5 pages).

Notice of Reason(s) for Rejection Dated Jul. 30, 2024 From the Japan Patent Office Re. Application No. 2021-576518 and Its Translation Into English. (11 Pages).

Hearing Notice Dated Feb. 14, 2025 From the Government of India, Intellectual Property India, The Patent Office Re. Application No. 202227002648. (4 Pages).

Notice of Reason(s) for Rejection Dated Jan. 7, 2025 From the Japan Patent Office Re. Application No. 2021-576518 and Its Translation Into English. (9 Pages).

Communication Pursuant to Article 94(3) EPC Dated May 20, 2025 From the European Patent Office Re. Application No. 20835138.7 (6 Pages).

Requisition by the Examiner Dated May 30, 2025 From the Innovation, Science and Economic Development Canada, Canadian Intellectual Property Office Re. Application No. 3,143,314. (3 Pages).

Pre Appeal Examination Dated Jun. 27, 2025 From the Japan Patent Office Re. Application No. 2021-576518 and Its Translation Into English. (6 Pages).

* cited by examiner

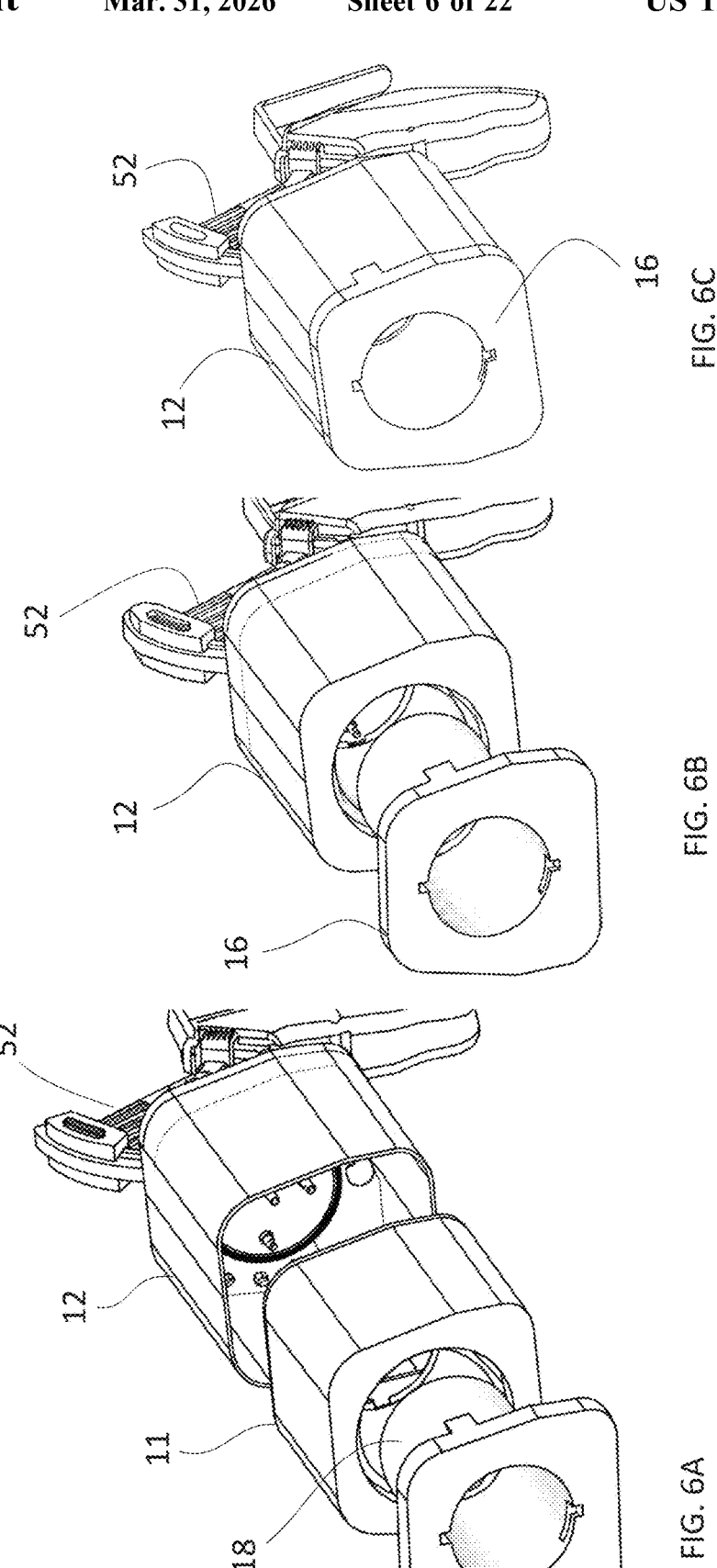

310
330
320
FIG. 13B
310
300
FIG. 13D
300
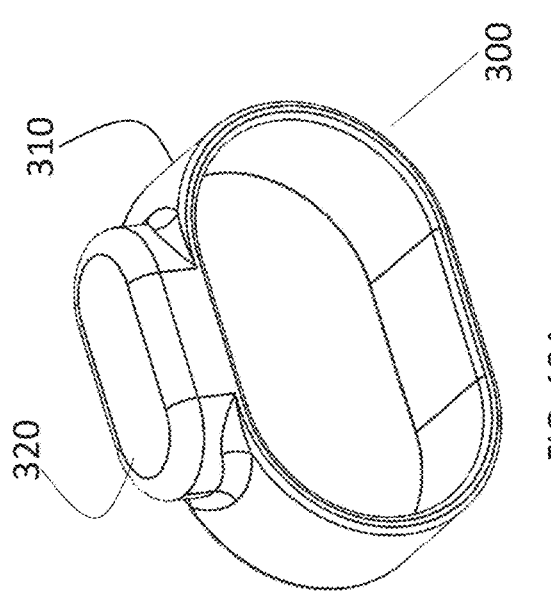
320
FIG. 13A
300
339
338
336
334
332
330
FIG. 13C
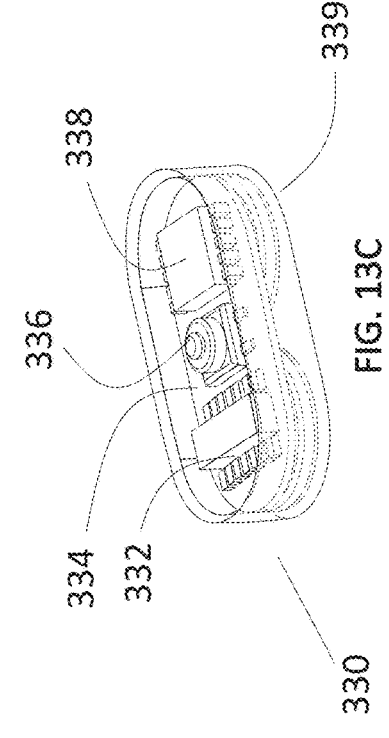

STERILE BARRIERS AND SENSOR SETS FOR A MEDICAL DEVICE

RELATED APPLICATIONS APPLICATION/S

This application is a National Phase of PCT Patent Application No. PCT/IL2020/050728 having International filing date of Jun. 30, 2020, which claims the benefit of priority under 35 USC § 119(e) of U.S. Provisional Patent Application No. 62/868,940 filed on Jun. 30, 2019. The contents of the above applications are all incorporated by reference as if fully set forth herein in their entirety.

FIELD AND BACKGROUND OF THE INVENTION

The present invention relates to medical devices having sterile barriers and sensor sets and related algorithms for controlling and tracking movements of device components and user.

Medical devices, especially surgical devices, must remain sterile during use in order to minimize the risk of infection or other contamination to the patient.

Medical devices having internal parts and mechanisms are difficult to clean and sterilize and can pose a health risk especially if the device or its internal components (e.g. sensors, motor packs) are used in more than one procedure. Without disassembling, cleaning and sterilizing the exterior parts of the device, and then re-assembling the device, it is difficult to maintain sterility of such devices. Furthermore, internal components such as sensor and motor packs are sensitive and oftentimes cannot be sterilized or repeatedly sterilized.

Barriers, such as tubular sheaths, that can prevent contact between the non-sterile parts of a medical device and the patient are known in the art. However, such barriers do not adequately shield internal components and moving parts that are capable of transmitting infective particles to the patient.

There is thus a need for medical devices having sterile barriers that protect internal components and moving parts and eliminate the need for re-sterilization of an internal component or an entire device.

SUMMARY OF THE INVENTION

According to one aspect of the present invention there is provided a medical device having compartments that enable loading and securing motor packs, internal parts, sensors, electrical circuits and/or control interface sensors.

According to another aspect of the present invention there is provided a sterile barrier between the contained parts and the sterile end effector, were the sterile barrier reduces the possibility of contamination of the sterilized end effector while allowing transfer of forces and moments from the internal parts to the end effector.

According to another aspect of the present invention there is provided a medical device having a sensors pack that can measure the movement of the control interface operated by the surgeon while correlating between the sensor pack and portions of the device and user.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 6A, 6B and 6C illustrate assembly of the present motor unit.

FIGS. 13A, 13B, 13C and 13D illustrate a sensors pack-carrying wrist bracelet.

DESCRIPTION OF SPECIFIC EMBODIMENTS OF THE INVENTION

Figure 1:
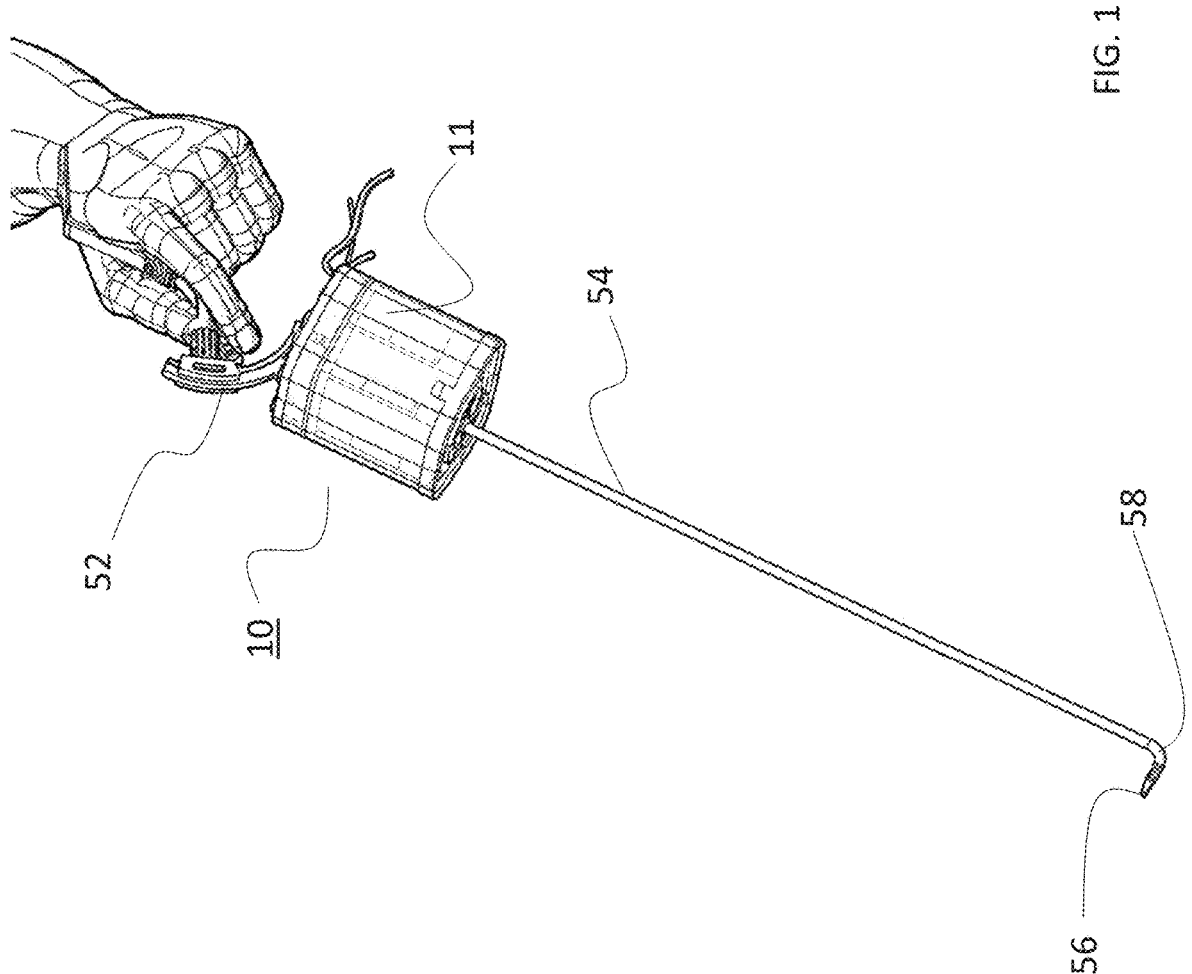
FIG. 1 illustrates an embodiment of a motor unit connected to an interface and tool shaft.

The present invention is of devices having sterile barriers that isolate internal components from the patient and environment and as such, allow reuse of such internal components without sterilization.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Sterile barriers for medical devices are well known in the art and typically take the form of sheaths/covers that cover an entire device or components that come in contact with the patient.

While such sheaths are somewhat effective in preventing patient contamination, they are oftentimes ineffective in preventing contamination of internal components that are either reused or are a part of a reusable device. Since internal components such as sensors, electric components and motor packs are sensitive and can be damaged by some forms of sterilization, sterilization of these reusable components is typically carried out via manual cleaning with antiseptic fluids, a time consuming and laborious task that can be unsuccessful in completely eradicating pathogens and contaminants.

Several paths of infection exists in medical devices:

(i) The motor pack (or another internal component) can transfer contaminants to the end effector when the pressure in the body cavity is less than the pressure in the motor pack.

(ii) The end effector can transfer contaminants such as blood to the motor pack (or another internal component) when the pressure in the body cavity is greater than the pressure in the motor pack.

(iii) Cycle of (i) and (ii) when pressure differences between body cavity and outer atmospheric alternate.

A sterile barrier can eliminate the need for sterilizing internal components or entire devices. Embodiments of the present invention relate to surgical devices having sensors and motors packs that are isolated from device components that come in contact with the patient (end effector) and as such, do not need to be sterilized while being incapable of transmitting pathogens and contaminations to the patient.

While reducing the present invention to practice, the present inventors have devised several sterile barrier configurations that can be used in a medical device to isolate internal components that are not easily serializable from the patient and from components of the device that come in contact with the patient.

As is describe hereinunder, these barriers can be used to isolate motor packs and batteries as well as sensors packs from the environment and from potential contamination by pathogens and contaminants. As such, these barriers enable reuse of internal components without a need for sterilization between uses.

Several barrier configurations are contemplated herein. Such configurations can be used in any medical device having internal components such as motor and sensor packs and batteries. Depending on use and device type, a medical device can incorporate one or more of these barriers.

The following describes the sterile barriers of the present invention in context with a surgical device (laparoscope) having a user interface connected to a steerable shaft having an end effector. It will be understood that the sterile barriers of the present invention can also be used with medical devices such as endoscopes, laparoscopes or catheters.

Motor Pack

While experimenting with several prototypes, the present inventors discovered that a motor pack that is engaged in serial manner greatly increased the length of the device body. In addition, serial engagement between the electronic pack and motor also increased the length of the device body. To solve these problems, the present inventors positioned the motor pack of the present invention such that it surrounds the instrument gear box with the motors, the electronic boards and the batteries positioned around the gear box (the gear box is positioned within the motor pack) to thereby substantially decrease the overall length of the device body and device.

FIGS. 1-9B illustrate the motor pack and associated components, collectively referred to herein as motor unit 10. Motor unit 10 can be integrated into a device 50 (laparoscope 50 shown) that includes a user interface 52 and a shaft 54 having an end effector 56 (grasper 56 shown) positioned at a distal end 58 of shaft 54. Shaft 54 can be rigid or steerable. Examples of steerable shafts are described in US20150366572 which is fully incorporated herein by reference.

Motor unit 10 includes a removable shell 12 that is externally sterile (and may be re-sterilized) and is dimensioned for encasing a motor pack 11. Shell 12 includes a shell body 14 and a front cover 16. Shell 12 is fabricated from PPSU or PEEK or PSU+Silicone (for reusable) and is typically 80-140 mm in length, 50-100 mm in width and 50-100 mm in height. Shell 12 isolates motor pack 11 from the environment and thus prevents any migration of contaminants or pathogens beyond the walls of shell 12.

Figure 2:
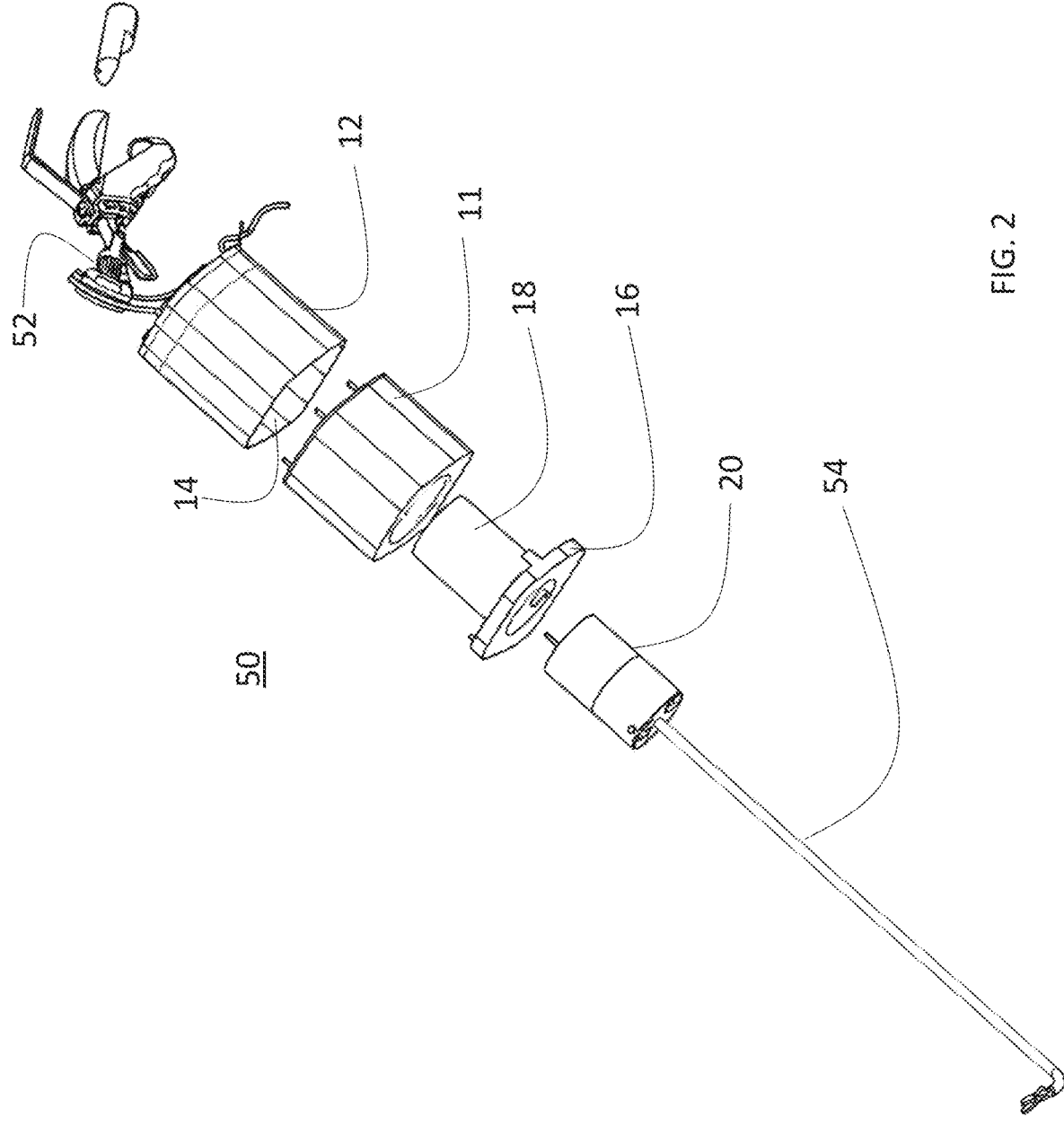
FIG. 2 illustrates the components of the motor unit of FIG. 1.

FIG. 2 illustrates the arrangement of motor pack 11 and shell 12. Motor pack 11 is positioned inside shell body 14, front cover 16 is attached to shell body 14 with cylindrical component 18 positioned through motor pack 11. FIGS. 6A-C illustrate assembly of motor unit 10.

An instrument adaptor and gearbox 20 (attached to shaft 54) is attachable within cylindrical component 18 of front cover 16 and interfaces with motor pack 11 through adapters provided in shell 12 (described hereinunder). Instrument adaptor and gearbox 20 is unique to the tool shaft used and varies between different types of tools but is connectable to any motor unit 10.

Figures 3A, 3B:
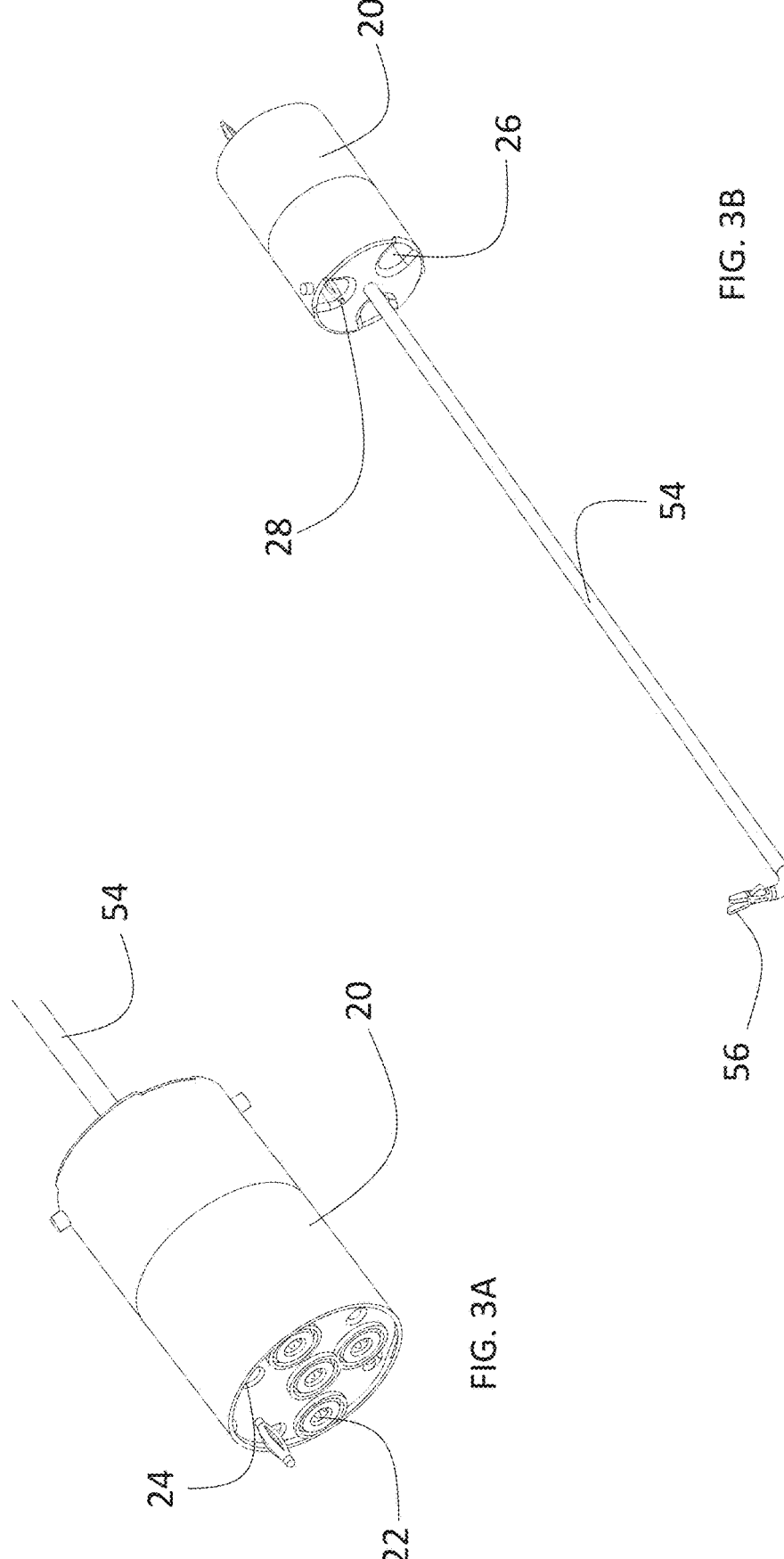
FIGS. 3A and 3B illustrate an instrument adaptor and gearbox connectable to the motor unit of the present invention.

FIGS. 3A-B illustrate instrument adaptor and gearbox 20 in more detail. FIG. 3A illustrates the shell-interfacing end of instrument adaptor and gearbox 20 showing sterile adapters 22 and optional end effector energy connector 24 (monopolar type connector shown). Insert guides 25 are provided to align instrument adaptor and gearbox 20 with motor pack 11. FIG. 3B illustrates the shaft side of instrument adaptor and gearbox 20 showing finger holds 26 that can be grasped by the user when connecting instrument adaptor and gearbox 20 to shell 12 and an optional end effector energy connector 28.

Figure 4B:
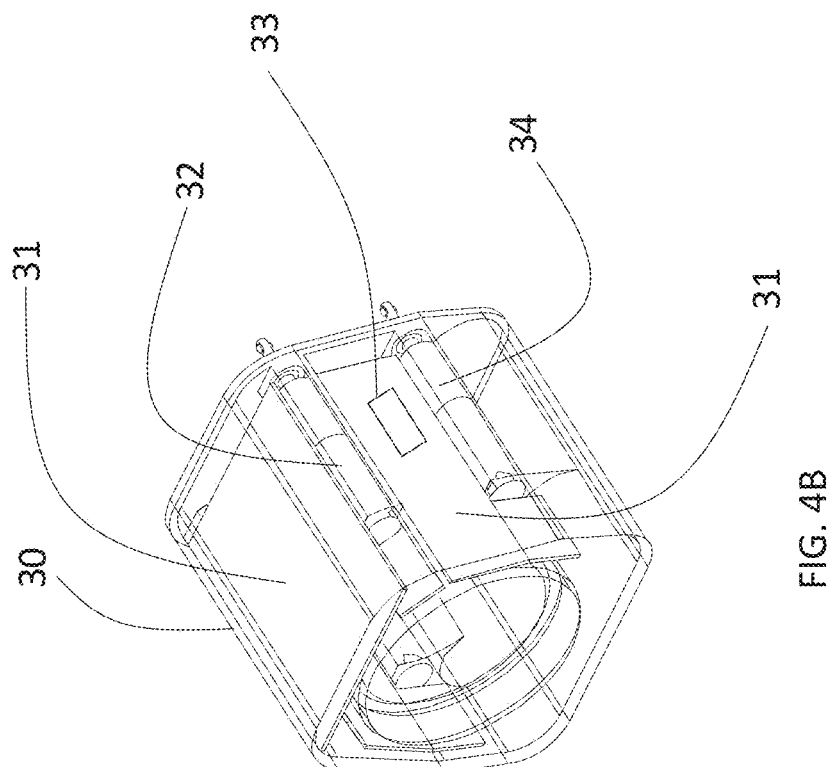
FIGS. 4A and 4B illustrates a motor pack component of the present motor unit.
Figure 4A:
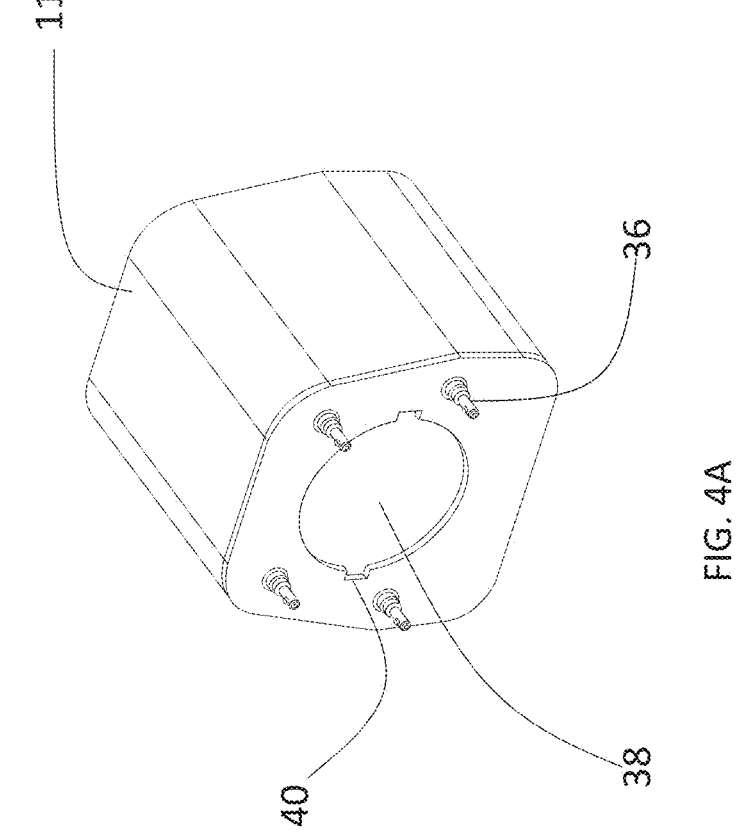

FIGS. 4A-B illustrate motor pack 11 including cover 30 and internal components. Motor pack 11 includes one or more of motor 32 and associated gear 34 (four shown). Gear 34 terminates in a protruding motor head 36 that interfaces with adapters within shell 12 (further described below). Motor heads 36 (best shown in FIG. 4A) are pushed into adapters for coupling.

Motor pack 11 includes an opening 38 for accepting (cylindrical) component 18 of front cover 16. Slots 40 are provided for guiding the instrument into the shell and lock it. At least IMU chip 33 is installed on electrical circuits boards 31.

Figure 5B:
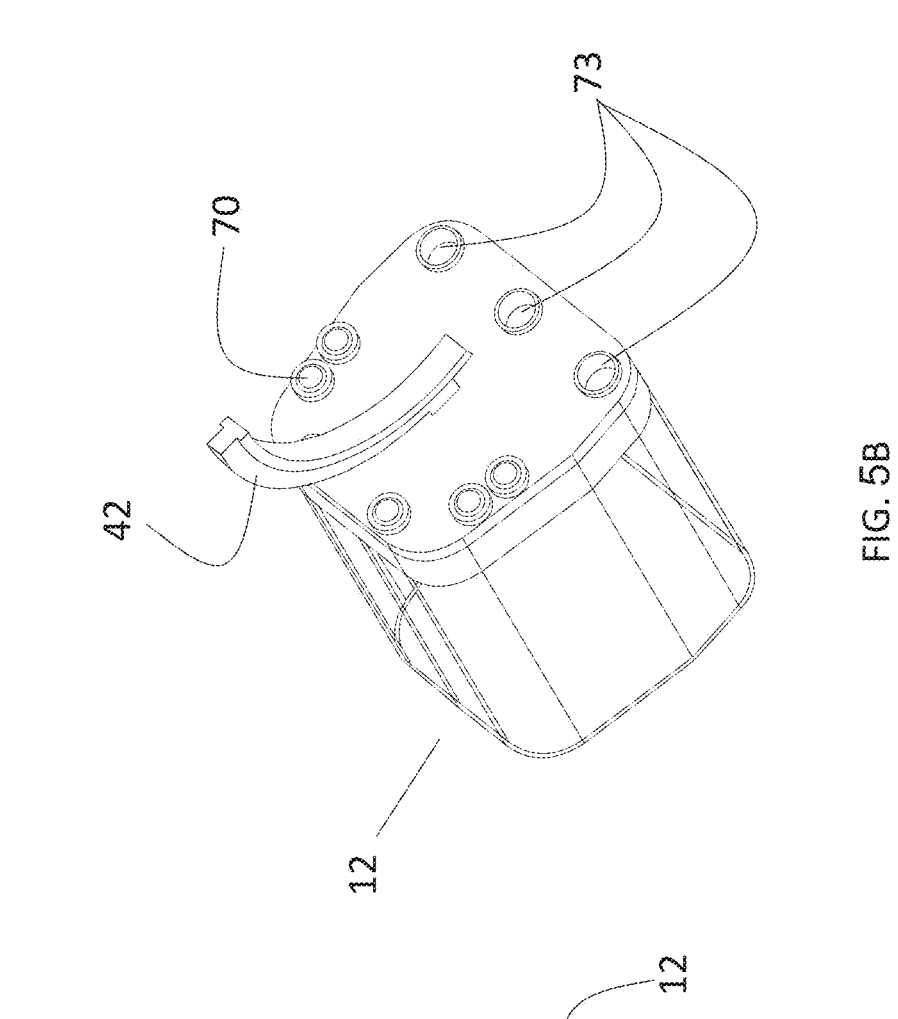
FIGS. 5A and 5B illustrate the sterile shell component of the present motor unit.
Figure 5A:
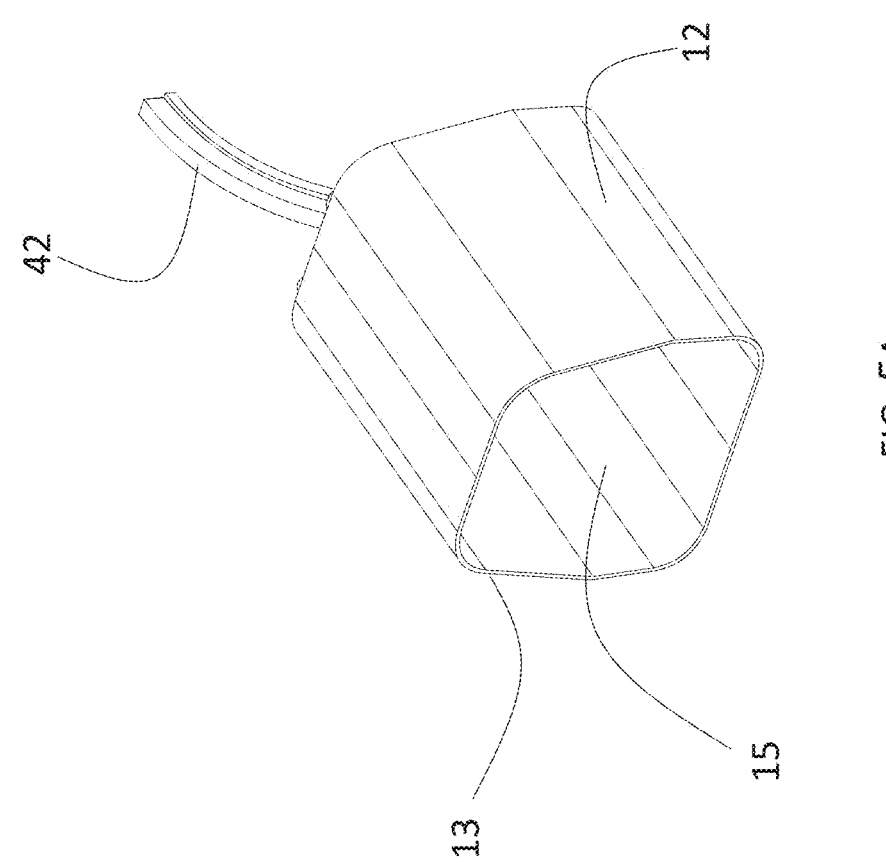
Figures 7A, 7B, 7C:
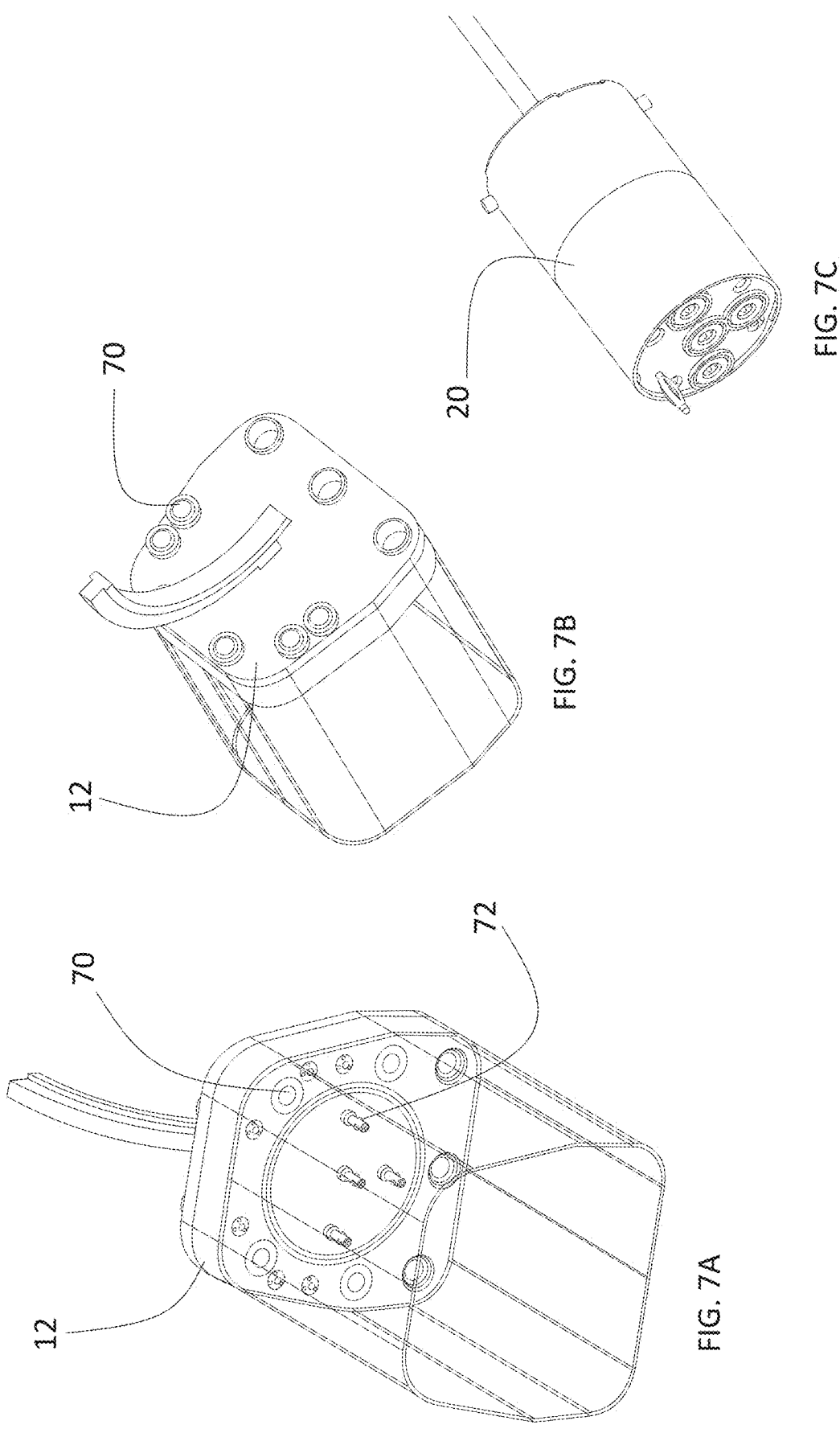
FIGS. 7A, 7B, 7C and 7D illustrate the motors and gearbox interfaces of the shell of the present motor unit.
Figure 7D:
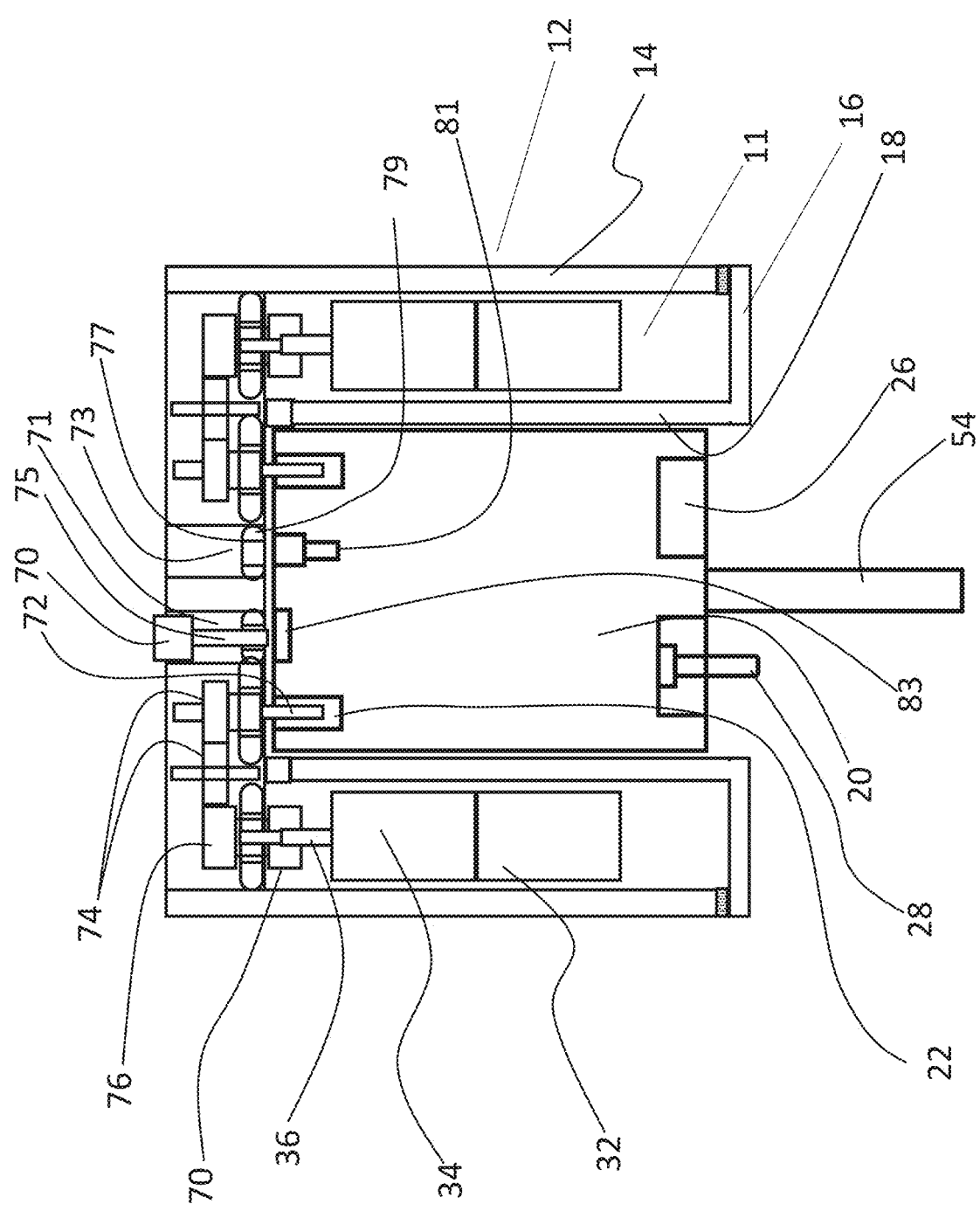

FIGS. 5A-B illustrate shell 12 in greater detail. The backside (facing the user) of shell 12 includes an interface rail 42 that allows the surgeon to move user interface handle 52, to the best ergonomic angle, and several mechanical push buttons and channels 71 that contain mechanical push rod 75 that transmit the push forces through the shell to sensors located at the motor pack. (The sensors may be capacitive, optical or mechanical). By pushing head button 70 (shown also in FIG. 7B), of push rod 75, the surgeon may select modes such as jaws speed of rotation, jaws angle of rotation, control mode etc. The ports 73 may be used for connecting external different types of cords, such as motor unit power cord, or energy cords (monopolar, Bipolar), to motor pack 11, through shell 12. Shell 12 includes a shell wall 13 and an opening 15 for accepting motor pack 11.

FIGS. 7A-D illustrate the interfaces for motor pack 11 and instrument adapters of gearbox 20 within shell 12. Push buttons 70 activate sensors 83 located in motor unit 11 by pushing rods 75. Internal openings 77 of ports 73 contains a seal 79, (e.g., O-ring), that enables connecting of external cords to motor unit 11 while keeping the motor unit insulated from the sterile environment. For example, external power cord will be connected to power connector 81 located in motor unit 11 through opening 73, while seals 79 ensures that the other external parts of the power cord will not be contaminated by the power cord distal plug. Motor heads adapters 76 transfer rotation of motor heads 36 to drive train transmitting motor moment to gear train distal heads 72. Distal heads 72 engages with adapters 22 of gear box 20 of the instrument, enabling the control of the instrument end effector jaws and the articulation.

When the shell and the motor pack are fully engaged the heads of the mechanical mode switches are positioned near sensors 83 which they activate. When the surgeon presses on one of the heads 70 of mode buttons, the distal head of the push rod 75 moves toward the motor pack and activates the designated mode sensor, and the desired mode is selected.

Figures 8A, 8B, 8C:
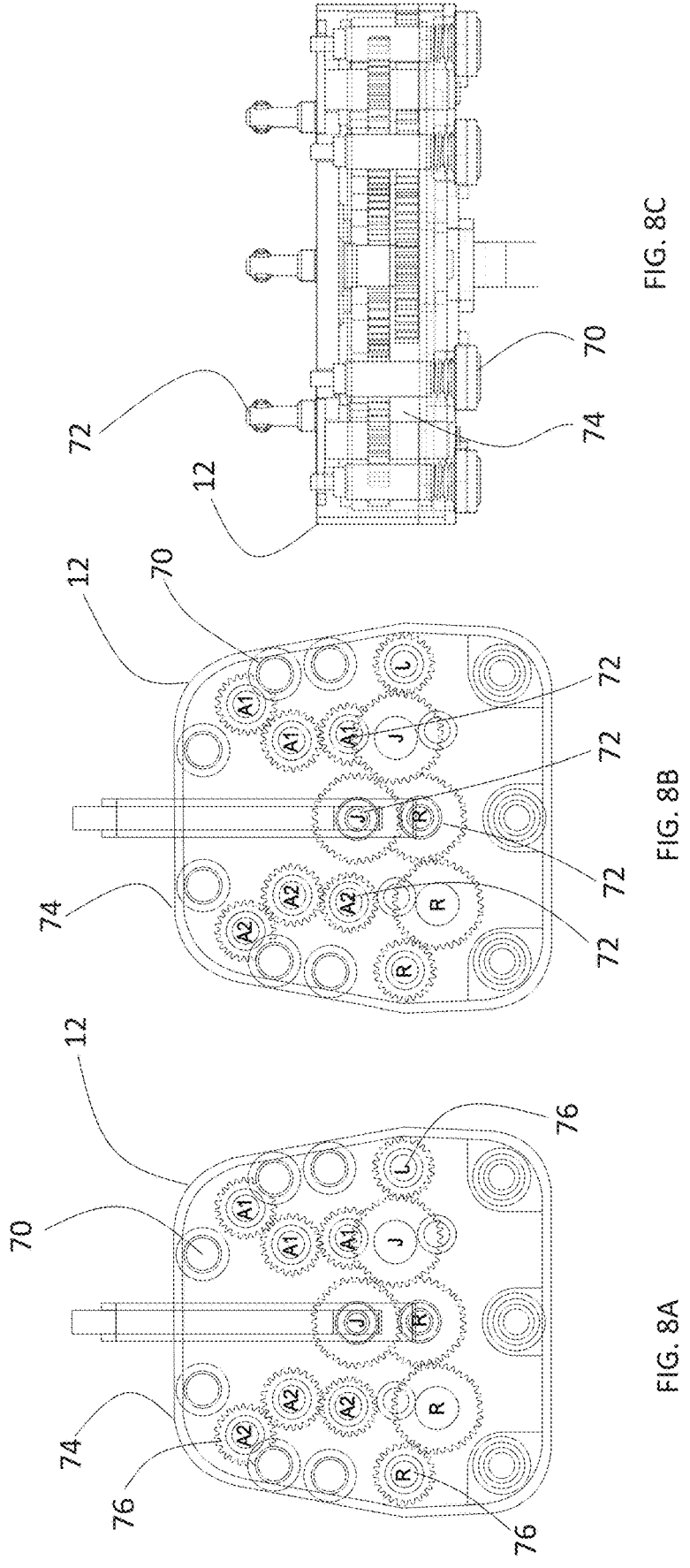
FIGS. 8A, 8B and 8C illustrate the drivetrain interconnecting the motors heads to the gearbox of the instrument adaptor and gearbox component.
Figures 9A, 9B:
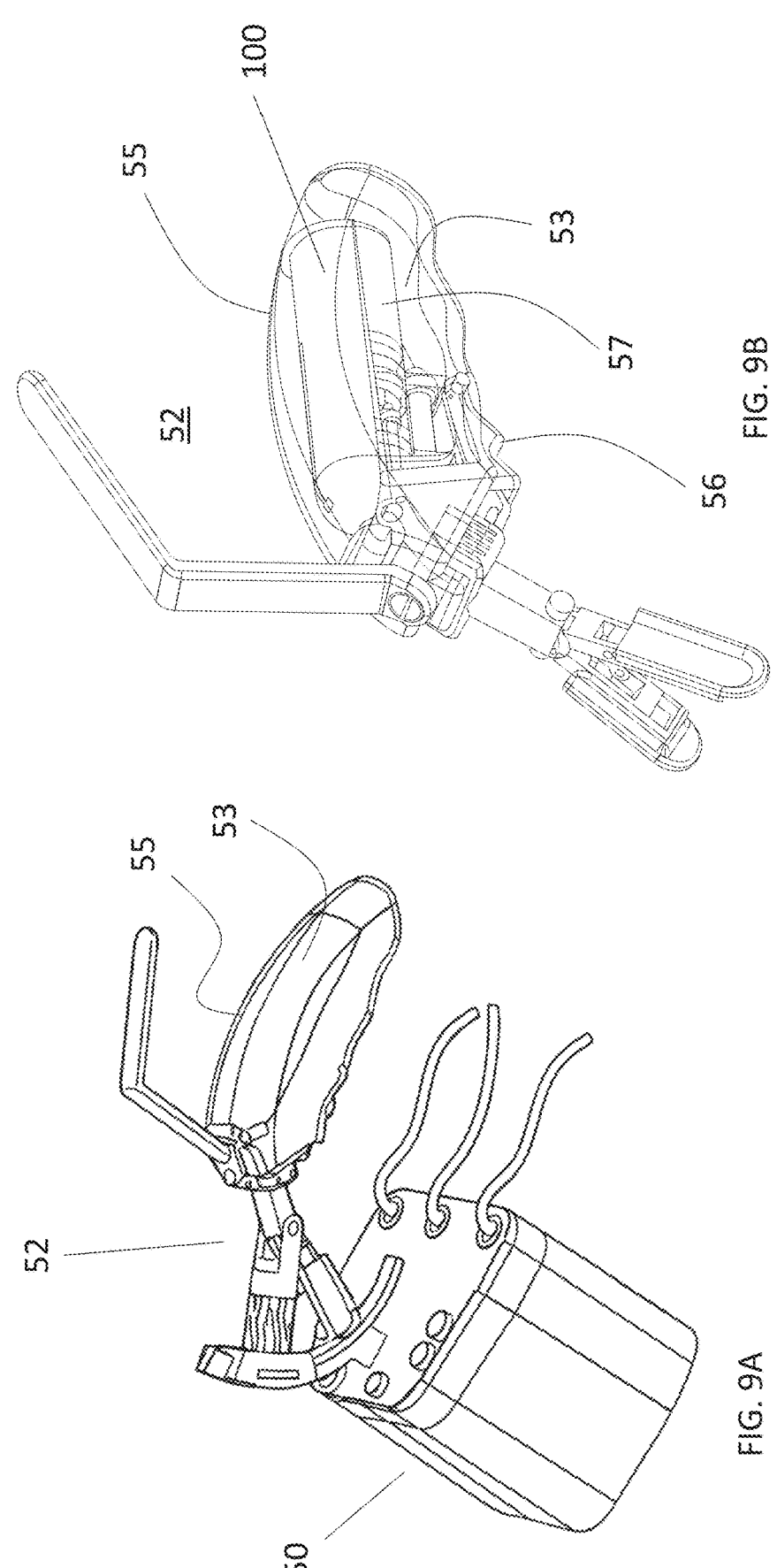
FIGS. 9A and 9B illustrate a user interface attached to the shell of a medical device (FIG. 9A) showing the sensors pack positioned in a housing of the user interface (FIG. 9B).

FIGS. 8A-C illustrate a drivetrain 74 that includes a plurality of gears for interconnecting between motor head adapters 76 and instrument head adapters 72. The drive train may be an integral part of the shell or a separate module connected to the shell. The drive train transfers rotation of the motors from the motor pack to the surgical instrument. The gear drive train allows the manufacturer to adapt the device to various of present or future instruments, just by changing the gear drive train, without the need to change the motor pack. For example, for power tools such as staplers, clip appliers or vessel sealers, the gears diameter may be changed in order to increase the moments transferred to the power instrument adapters. For other instruments such as needle holder, hook or grasper, where fast movements are required the manufacturer may choose gear train that transfers faster rotation to the instrument. Some power tools with less degrees of freedom may need less motorized inputs, in this case, a gear train design, which combine 2 or more motors to a single output may be used. The gear train geometrical configuration may be also be changed in order to adapt to different geometries of instrument gear box.

FIGS. 8A-B show the shell of the motor pack and its inner side components. Four input adapters 76 that transmit the power from the motors into the gear trains in the shell are located at the corners of the shell. Gear trains transfer the motors movement to the output heads, arranged in a T formation, 3 instruments heads 72 in horizontal line and one instrument head under the central motor head.

FIG. 8B is an upper view of the shell and the gear trains. Each gear train is labeled as follows:

J gear train transfers the power from the motor pack to the jaws mechanism to enable open and close movement of the jaws.

R gear train transfers the power from the motor pack to the jaws mechanism to enable roll movement of the jaws.

A1 gear train transfers the power from the motor pack to the articulation, to enable up/down articulation of the shaft.

A2 gear train transfers the power from the motor pack to the articulation to effect right/left articulation of the shaft.

Sensor Pack

In order to control the instrument functions the present invention describe a control interface shaped to fit the hand of the surgeon allowing the surgeon to simultaneously position the end effector in the patient body, orient the control interface in order to control the bending of the articulation and operate the jaws. The control interface has 3 main components: the control interface body including fingers interface, the dorsum interface 59, and the handle which serves as a container to the sensors capsule.

This interface design enables re-sterilization of the control interface body, while eliminating the need to sterilize delicate electric components contained in the sensors capsule. The design also enables future upgrading of the electric circuits and sensors, contained in the sensors capsule without the need to make any change in the control interface body. In addition, the handle may be changed without the need to change the sensors capsule.

In order to ensure complete insulation between the electric circuits in the sensors capsule and the control interface body, the sensors capsule is sealed, and the sensors are insulated from their measurement reference.

For example, a Hall Effect sensor (such as Melexis) with a magnet which serves as the rotation measurement reference is embedded in the control interface body, and the Hall Effect sensors 120,130 (shown in FIG. 10B), are located in the sealed sensors capsule. Although there is no direct contact between the magnet and the sensor, the Hall Effect sensor is able to measure accurately the angle position between the sensor and magnet. The insulation concept is also valid for rotation potentiometer, where a stationary reference base may be coupled to the potentiometer rotor without exposing the sensor electric circuits to the control interface body.

FIG. 9A-11D illustrate one embodiment of the sensor pack of the present invention which is referred to herein as sensor pack 100.

Sensor pack 100 is position within a housing 53 of a user interface 52 (also referred to herein as controller or control interface) of device 50. As is shown in FIGS. 11A-D, sensor pack 100 is loaded into housing 53 by opening a hinged cover 55 and sliding sensor pack 100 into a recess 57 within housing 53. The sensor pack includes sensors that may sense continuously the orientation of the control interface with respect to the orientation of the motor pack, measured by similar sensors located in the motor pack.

Figures 12A, 12B:
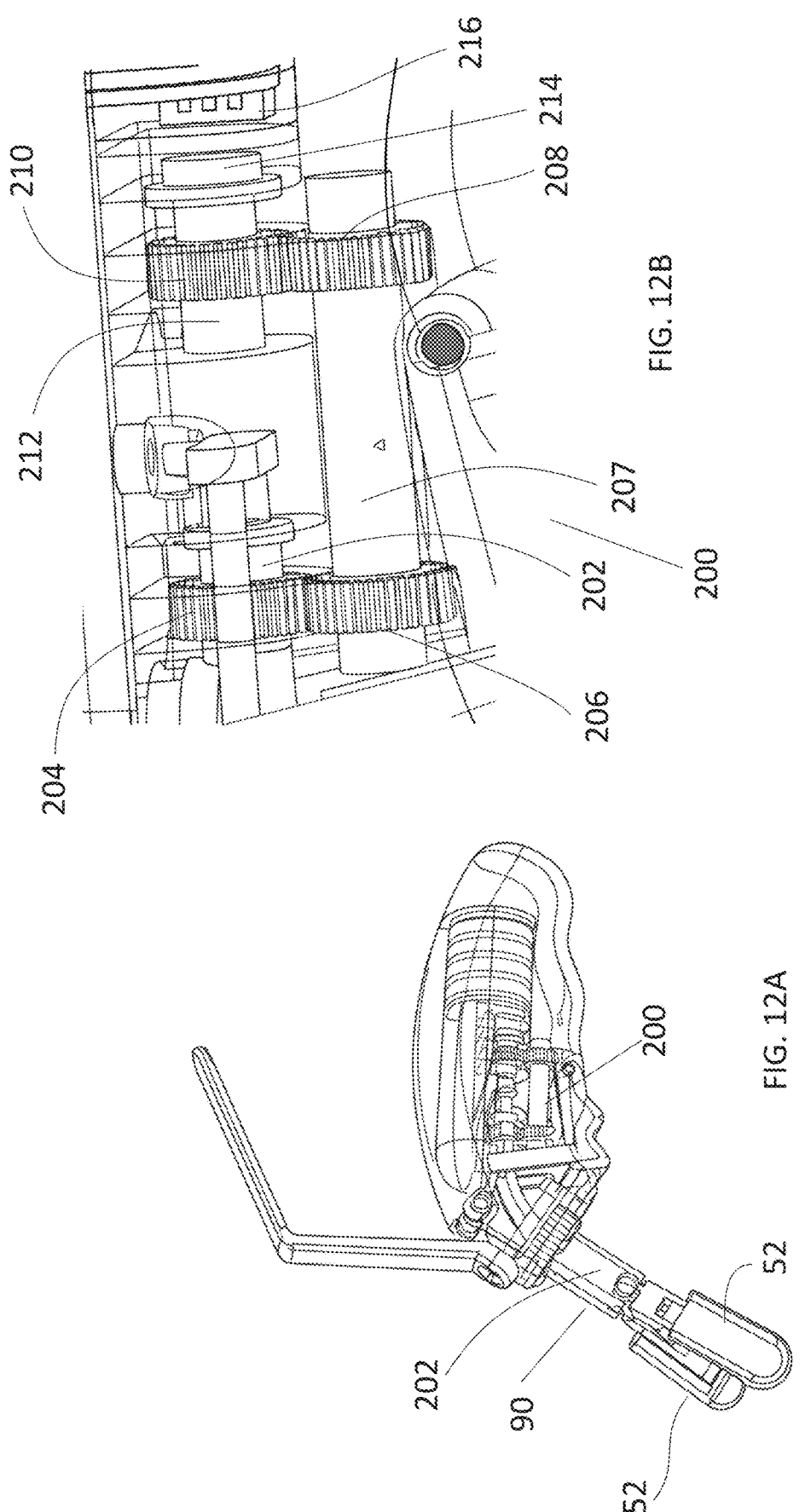
FIGS. 12A, 12B and 12C illustrate the finger interface mechanism of the user interface.
Figure 12C:
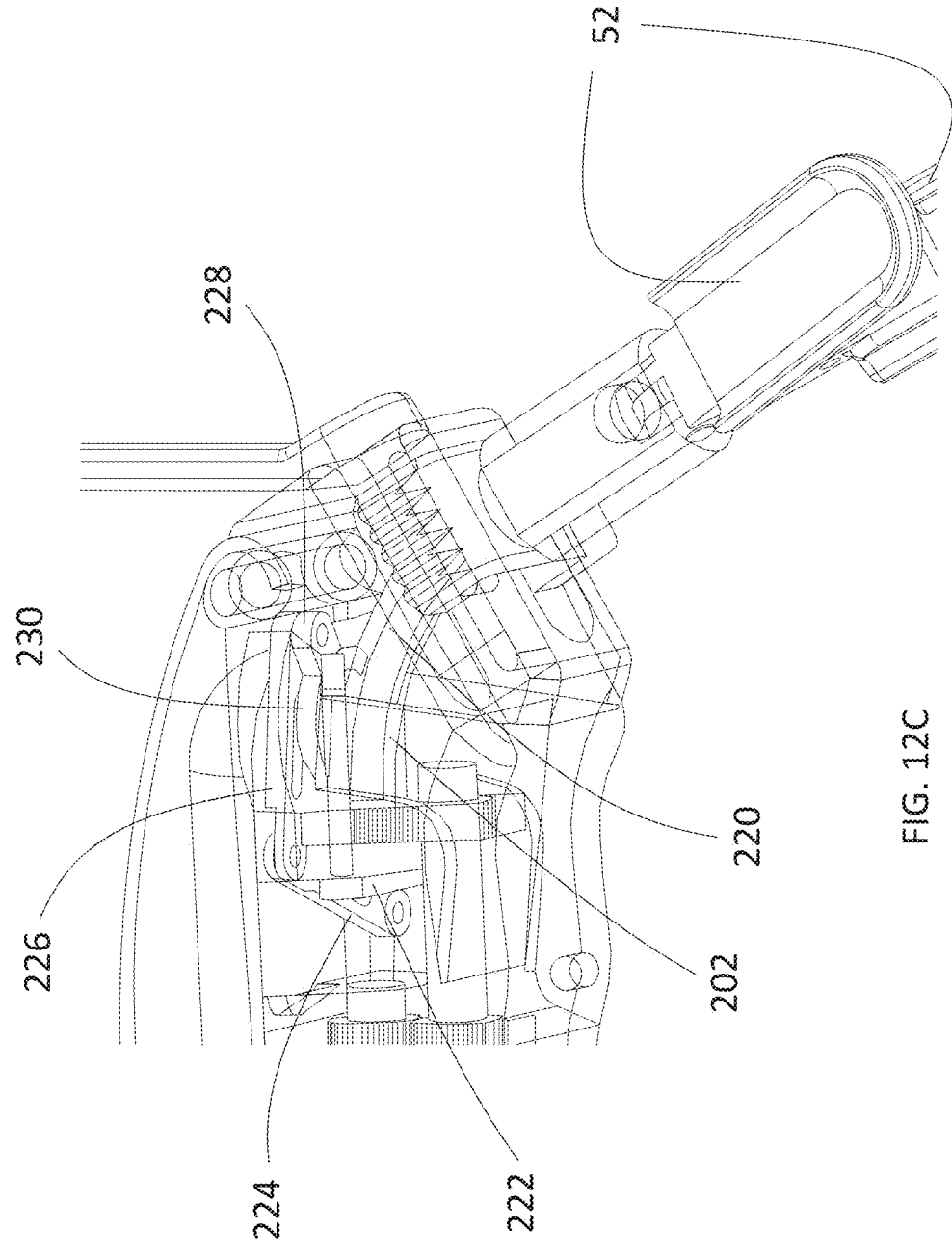

As is described above, sensor pack 100 may also include sensors 120, 130 that may sense movement of fingers. The fingers interface transfers finger motion to a magnet that serves as sensor references located near the sensors 120, 130 at the sensors pack. The sensors located in the sensors pack, measure the sensor reference rotations or translations as is shown in FIGS. 12A-C.

Sensor pack 100 may include independent energy source and wired or wireless connectivity (e.g., Bluetooth), in order to transmit data obtained by the sensors to the motor pack in order to control the instrument end effector. Sensor pack 100 may also include memory circuits.

Figures 10A, 10B:
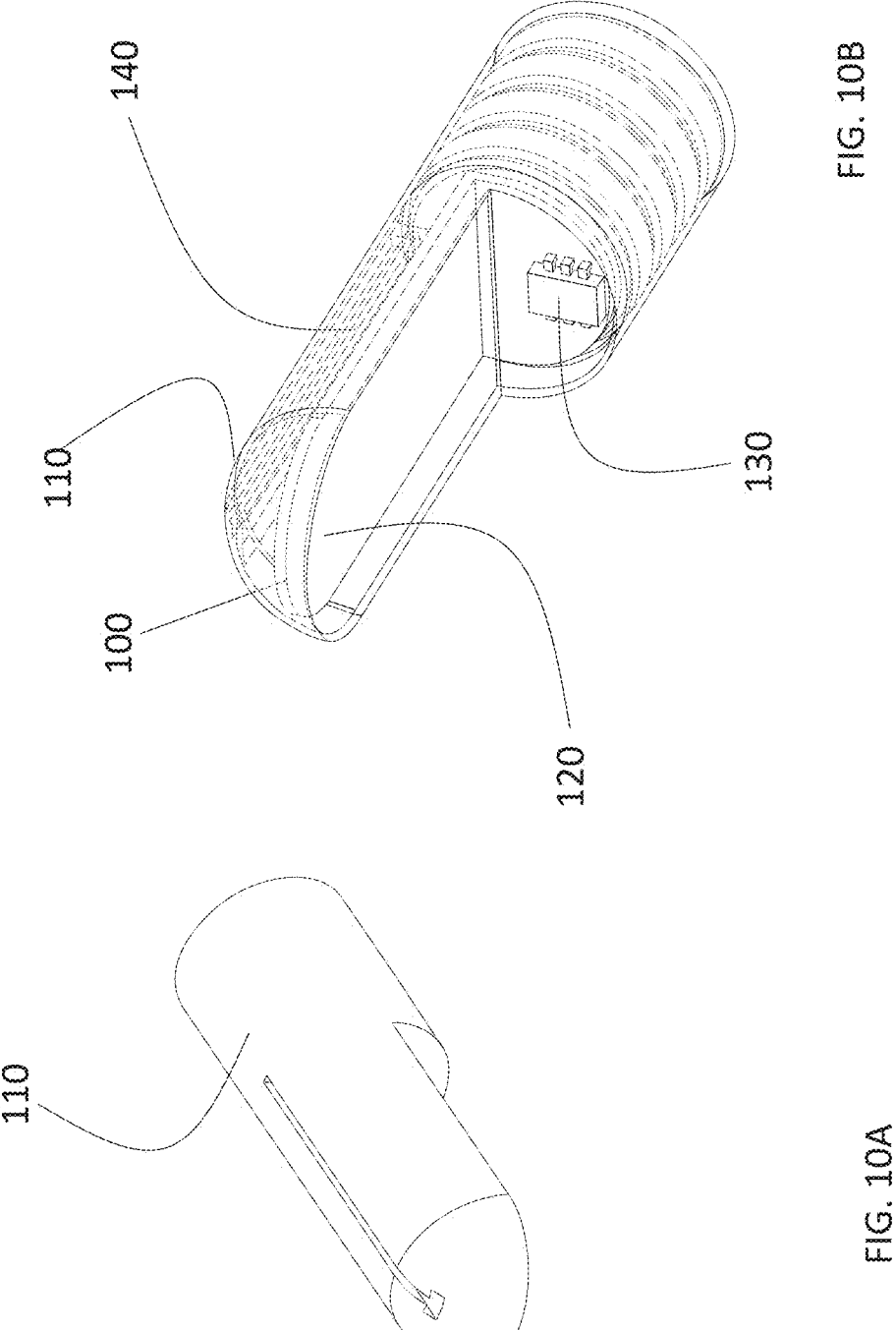
FIGS. 10A and 10B illustrate one embodiment of the present sensor pack.
Figures 11A, 11B, 11C, 11D:
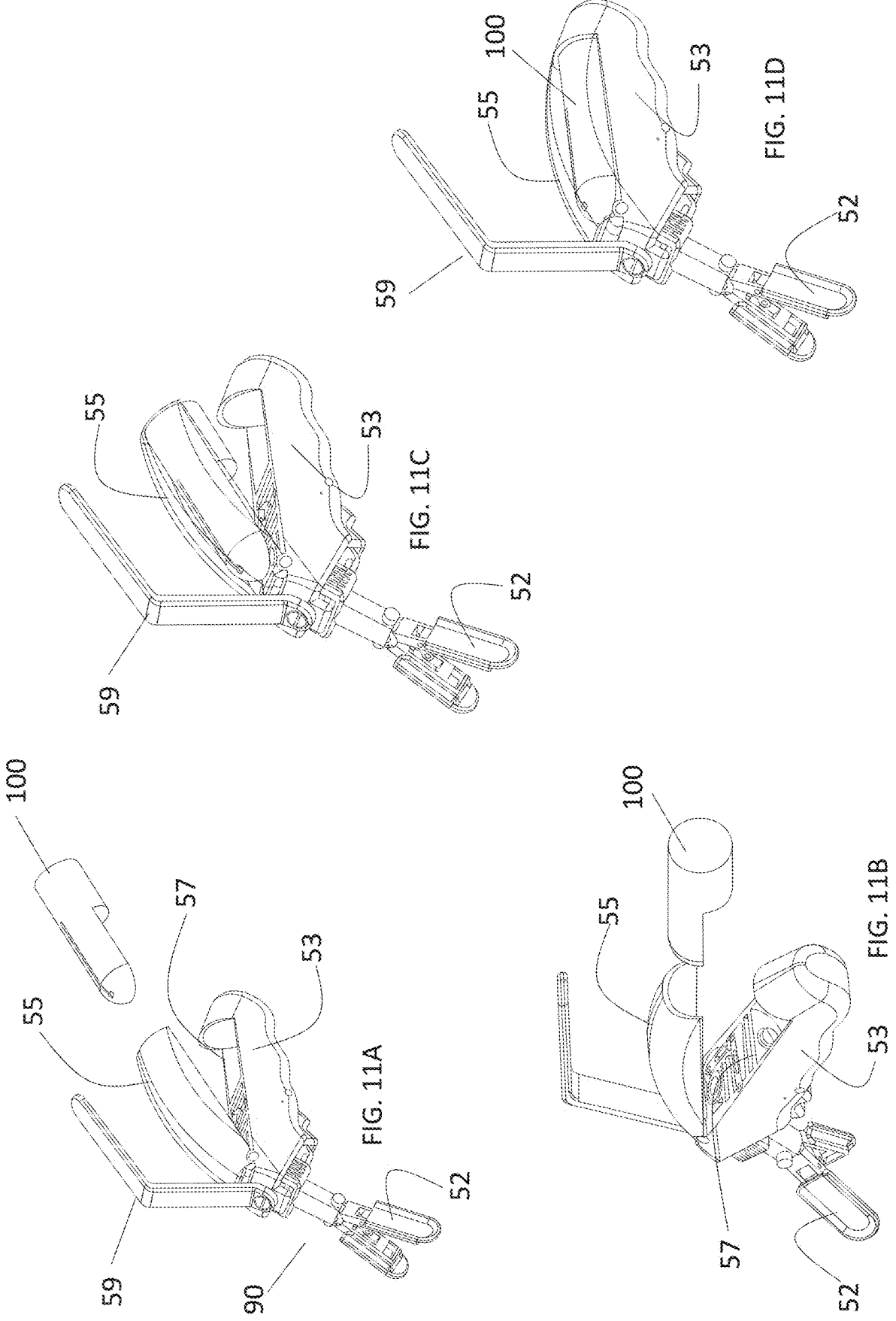
FIGS. 11A, 11B, 11C and 11D illustrate loading of the sensor pack into the housing of the user interface.

Sensor pack 100 is shown in FIGS. 10A-B. Sensor pack 100 is sealed within a capsule 110 made of materials such as Polycarbonate, ABS etc. The sensor pack may include 2 Melexis sensors. The 1$^{st}$ Melexis sensor 120, measures the angle between the fingers pads levers. This measurement controls the angle between the jaws of the end effector. The second Melexis sensor 130, measures the rotation of the fingers pads levers. This measurement controls the rotation of the end effector jaws. Sensors pack 100 can include at least one IMU (Inertial Measurement Unit) sensor 140. The Examples section below describes sensor function in greater detail.

Once positioned within recess 57 and cover 55 is closed, sensor pack 100 is sealed within housing and is isolated from the environment and patient.

Once sensor pack 100 is functionally coupled to device 50, the surgeon "wakes" the sensors capsule from sleep mode by pressing on the dialog button. Sensors pack 100 transmits a signal to the motor pack and "awakes" the motor pack from the sleep mode and the device is ready for use.

In order to use the device, the surgeon inserts the instrument into the patient body through a trocar, positions the instrument and activates the jaws and the articulation according to his needs. As is described herein, the fingers interface controls the roll and the jaws open/close action, while the control interface movements control the articulation deflection and orientation.

The measurement of the signals from the sensors located in the sensor pack and in the motor pack are sampled by control processor that may be programed to different modes of control. The mode of control is selected by the surgeon by sequence of pressing on the dialog button 56. The selected mode reflects the changing needs of the surgeon, in different phases of the procedure.

For example, when suturing the surgeon may prefer to deflect the articulation to any direction in order to preform knots, while in another surgical phase the surgeon might prefer to fix the articulation in a certain orientation with respect to the shaft, or to keep the articulation with fixed orientation in space in order preform a running suture.

If the surgeon is ergonomically uncomfortable, articulation can be frozen in a desired orientation enabling the surgeon to orient the control interface to a more preferred position. Articulation can then be un-frozen to reenable control of articulation.

The Examples section below describes the operation of the interface and associated sensors.

While the surgeon holds the control interface body and orients it, the fingers are in contact with finger pads 52 located at the distal end of finger interface 90. In order to measure the movements of the surgeon's fingers, finger interface 90 includes 2 mechanisms that may be operated simultaneously: a finger roll mechanism and a finger open/close mechanism.

Fingers roll and open/close interface mechanisms are located in the control interface body shown in FIG. 12A.

FIG. 12B shows in detail the Fingers roll mechanism. When the surgeon rotates finger pads 52, flexible shaft 202 rotates therewith. Gear 204 located in the handle is attached to the end of shaft 202. Gear 204 rotates gear 206 and gear 208 which are connected to the two ends of shaft 207. Gear 208 rotates gear 210 which rotates shaft 212. Magnet 216 is embedded in the end of shaft 212 and positioned in front of Hall Effect sensor 130, located in the sealed sensors capsule. When the surgeon rotates his/her fingers, the rotation movement is transferred by the gear train described above and sampled by the sensor located in sensor pack 100.

FIG. 12C shows in detail the fingers open/close interface mechanism. The surgeon controls the jaws open/close action and angle by controlling the angle between finger pads 52. When the surgeon presses on pads 52, the end of the finger's open/close shaft 220, located in flexible rotation shaft 202, moves linearly, when the surgeon closes pads 52 shaft 220 moves forward and when the fingers are released shaft 220 move backwards. Links train 222, 224, 226 and 228 converts shafts 220 linear motion to rotation of magnet house 230. The magnet is located at a sensing distance from another Hall Effect sensor 120, installed in sensor pack 100. The Hall Effect sensor 120, samples the rotation of the magnet, and the sensor readings serve as input for the device controller.

FIGS. 13A-D show in detail the IMU bracelet device. FIG. 13D shows the IMU bracelet device worn on the surgeon wrist. The IMU bracelet device may serve as reference measurement used for controlling and orienting the device end effector articulation as is described in detail below.

The IMU bracelet device 300, includes a strip 310 fabricated from rubber or any other flexible polymer. The strip is connected to the IMU device housing 320 as shown in FIG. 13A. The IMU device housing 320 includes the IMU device capsule 330 as shown in FIG. 13B.

FIG. 13C shows in detail the structure of the IMU device housing 330. The IMU device includes a PCB 334 with an IMU chip 332 and a wireless communication chip 338. An On/Off push button 336 is used to switch on the device and initiate the communication between the device and the control circuits in the device, and to start measuring the orientation of the IMU chip. The IMU 332 measurements, may be used to control the orientation of the end effector articulation as is described below. The IMU capsule device 330 includes rechargeable batteries 339 that are packed along with circuitry in a sealed capsule.

Figure 14:
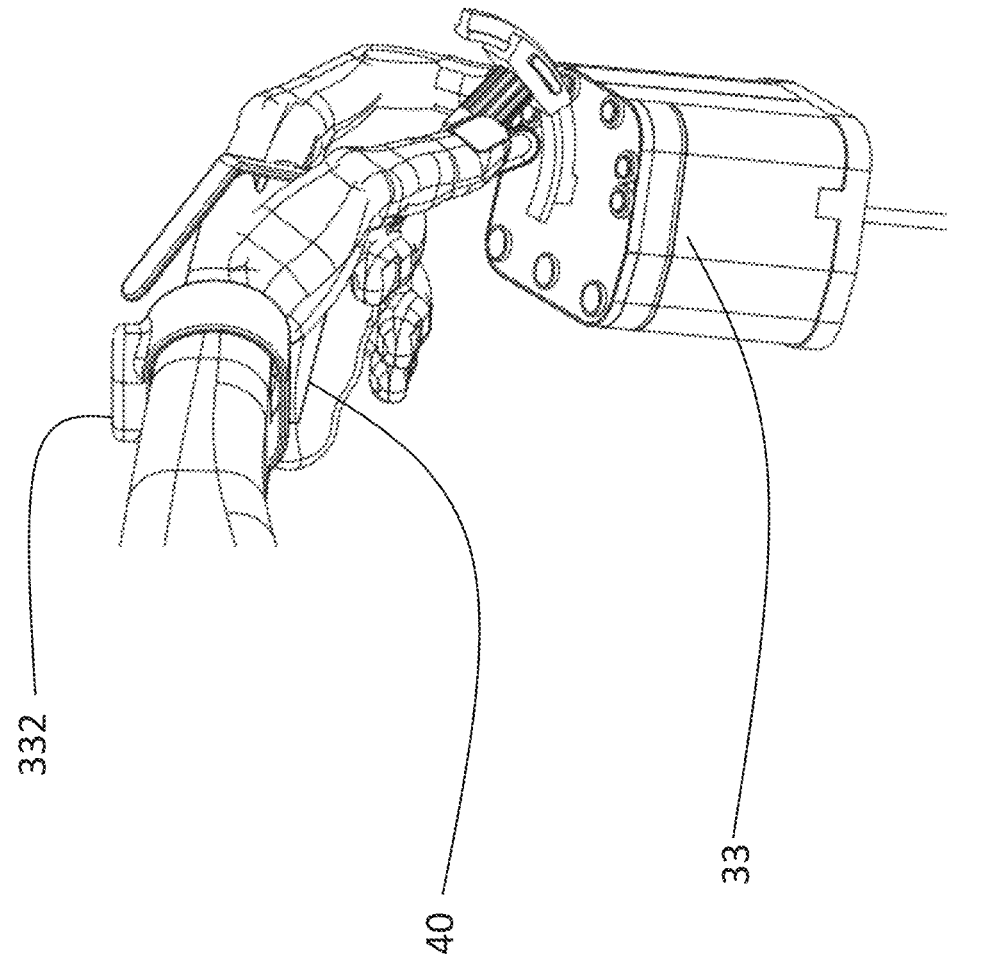
FIG. 14 illustrates possible sensor positions in and on the device and user.

FIG. 14 illustrates possible locations for various IMU devices a wrist IMU 332, a handle IMU 140 (located in sensors pack 100) and a device IMU 33 located in a portion of the surgical device (e.g., motor pack electric boards).

The signals from the IMU devices can be collected simultaneously by the main control circuits of the surgical device. The main control circuit may use a single IMU device or combination of IMU devices in order to calculate control commands for the motors that drive the articulation.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrate the invention in a non-limiting fashion.

Interface and Sensors

The following describes sensors and related algorithms that gets as an input, the movements of the device portions (interface, device body, shaft, tip, end effector) and the user hand, and, calculating as an output, control commands for the articulation member. The sensor set can include three IMU sensors positioned in the handle, and/or a wrist bracelet and/or device body (e.g. motor unit housing and shaft) and two pairs of relative sensors (potentiometers or the like) that may be positioned in order to measure the angles of the handle with respect to the device body and/or in order to measure the orientation of the handle with respect to the wrist of the user.

The above described sensor set can be reduced in number and yet still provide similar functionality. For example, the sensor set can be reduced to 3×IMU sensors in handle, wrist bracelet and device—no relative sensors, 2×IMU sensors in handle and device—no relative sensors, 2×IMU sensors in handle and wrist bracelet—no relative sensors, 1×IMU sensor in the handle and a relative sensor between the handle and device body or 1×IMU sensor in the device body and a relative sensor between the handle and device body.

Sensor Positions and Measurements

Figure 15:
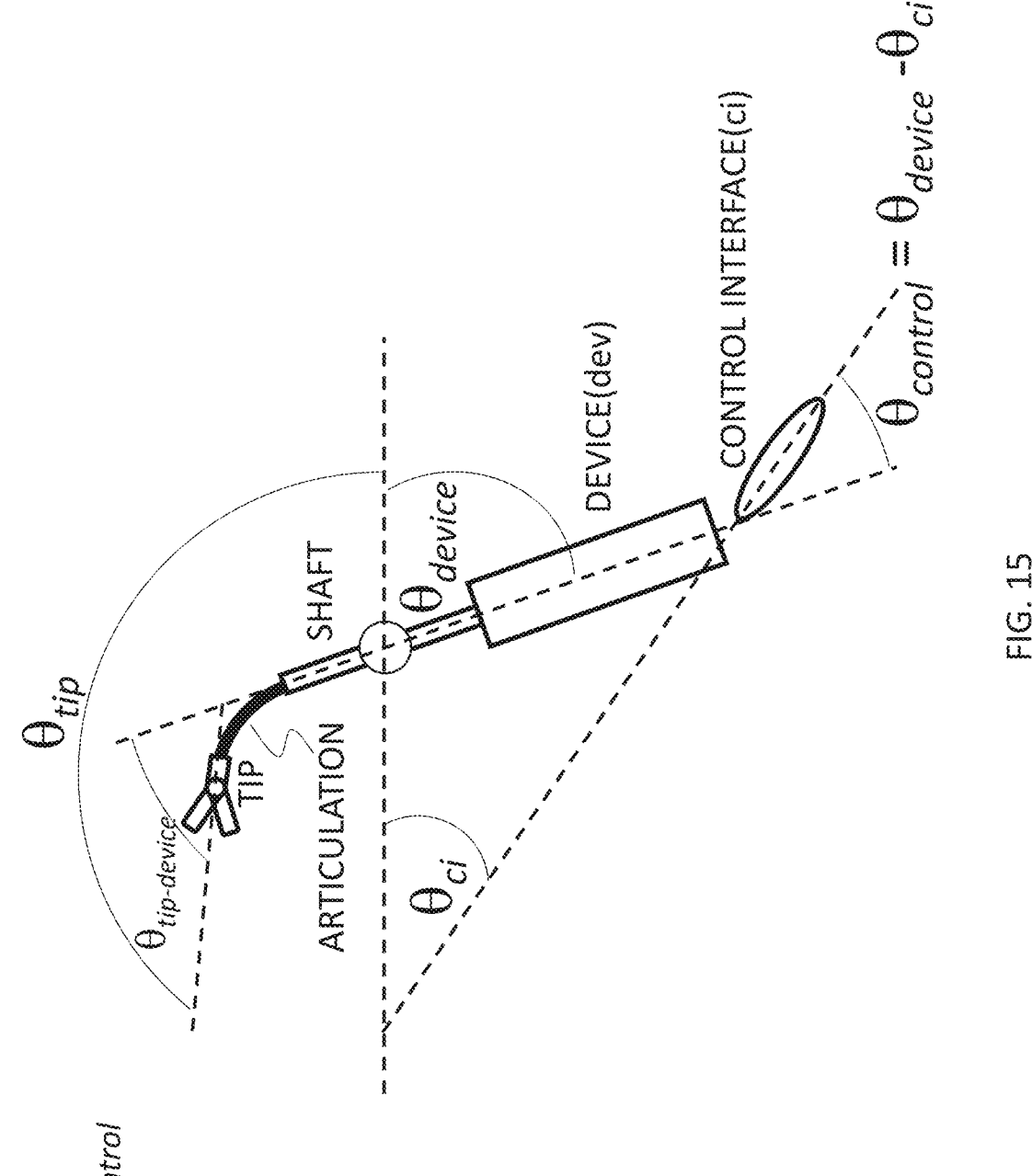
FIG. 15 illustrates the main components of the control interface of the device, the end effector and their related angles.

FIG. 14 schematically illustrates possible sensor positions. FIG. 15 details the parts and angles that are referenced herein.

The following measurements can be made by the sensor set:

(i) Relative measurement between handle and device can be achieved using the relative sensors or by calculating the difference between the handle and device's IMU sensors 33.

(ii) Relative measurement between handle and the user arm (wrist angle) can be achieved using the relative sensors or by calculating the difference between the handle and wrist wearable IMU 332 device sensors.

(iii) Relative measurement between device and the user arm can be achieved using the relative sensors in chain or by calculating the difference between the device IMU 33 and wrist wearable IMU 332 device sensors.

(iv) Absolute measurement handle, device or arm orientation can be achieved using IMU sensors 33, 140, 332.

(v) Combination of some or all IMU devices sensors.

Handle-Articulation Ergonomics Settings Mode

Handle-articulation settings mode may be used by the surgeon in order to achieve better ergonomics while using the device. When using trocars in laparoscopic procedures the position of the trocar may impose non ergonomic positions between the hand of the surgeon and the surgical device and shaft. The IMU devices allow the surgeon to re-position the handle with respect to the device body, in order to achieve an optimal ergonomic working environment.

When a surgeon wishes to re-position the control interface handle in order to achieve a better ergonomic position, the surgeon presses dialog button 56 (shown in FIG. 9B), and the device control circuits lock the articulation in its current bending position. If the user keeps pressing the dialog button, the user may move the handle to a desired ergonomic position, while the articulation bending position does not change. When the surgeon releases the dialog button, the handle orientation becomes the new control position for the current bending position of the articulation, and the new zero position and the orientation of the control interface coordinate system is re-calculated. Essentially, the surgeon can repeat this sequence any time during the procedure and configure the handle's coordinate system to his ergonomic needs.

An algorithm embedded in the control circuits transforms the sensors' inputs to the desired articulation bending.

The setting described above, can be implemented at the sensor level as follows:

let the relative yaw, pitch and roll angles between the handle and the device be $\{y, p, r\}$. A user sets a new coordinate system at relative angle $\{y_0, p_0, r_0\}$ by positioning the shaft at a desired handle-device orientation. A transformation matrix is then set as follows:

$$T = \begin{bmatrix} C(p_0)C(r_0) & S(y_0)S(p_0)C(r_0)+C(y_0)S(r_0) & -C(y_0)S(p_0)C(r_0)+S(y_0)S(r_0) \\ -C(p_0)S(r_0) & -S(y_0)S(p_0)C(r_0)+C(y_0)S(r_0) & C(y_0)S(p_0)C(r_0)+S(y_0)S(r_0) \\ S(p_0) & -S(y_0)C(p_0) & C(y_0)C(p_0) \end{bmatrix}$$

The relative angle between the handle and device will be shifted:

$$\begin{bmatrix} y_i \\ p_i \\ r_i \end{bmatrix} = \begin{bmatrix} y \\ p \\ r \end{bmatrix} - \begin{bmatrix} y_0 \\ p_0 \\ r_0 \end{bmatrix}$$

The transformed output to the articulation bending is calculated:

$$\begin{bmatrix} y_1 \\ p_1 \\ r_1 \end{bmatrix} = T \begin{bmatrix} y_i \\ p_i \\ r_i \end{bmatrix}.$$

Figure 16:
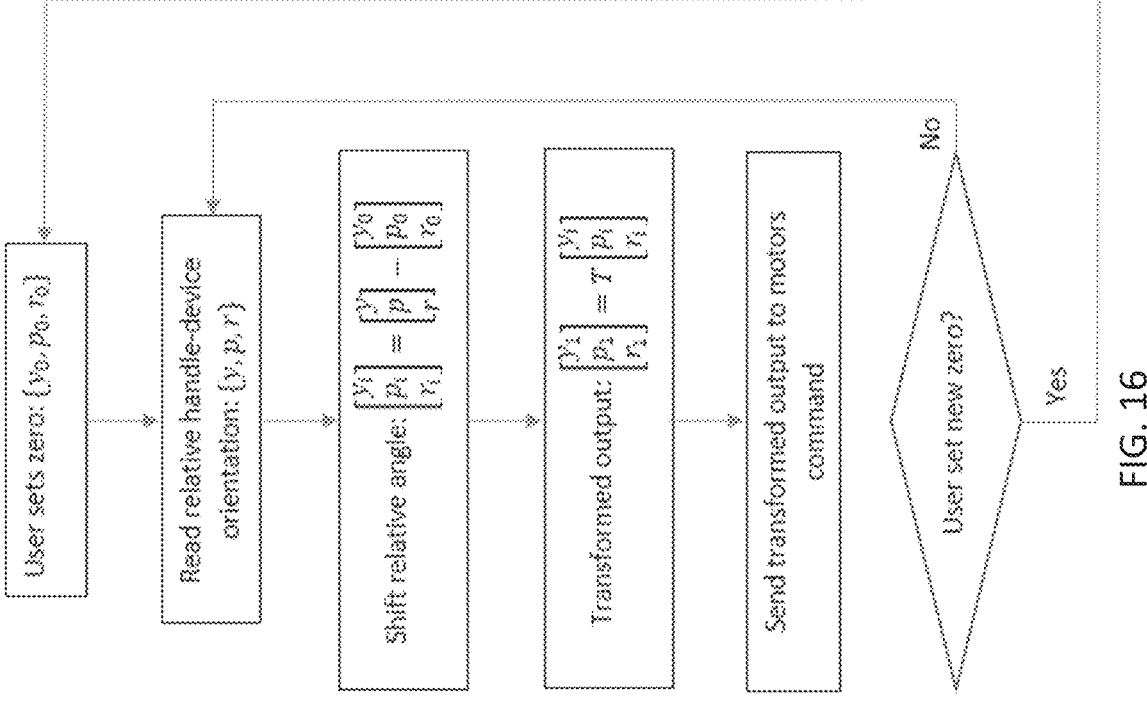
FIGS. 16, 17, 18, 19 and 20 are flowchart diagrams illustrating several calibration and set up functions for device control and tracking.

FIG. 16 is a flowchart diagram describing this process.

Articulation Stabilization Mode

Referring now to a control mode where the articulation bending is calculated by the difference between the spatial angle of the control interface and the spatial angle of the device:

$$\theta_{Control} = \theta_{device} - \theta_{ci}$$

$\theta_{Control}$ includes an unknown $\theta_{parasitic}$ resulting from changes in the orientation and position of the device while the surgeon moves the device. The stabilization function measures the parasitic angle ($\theta_{parasitic}$) and cancels this parasitic motion by subtracting $\theta_{parasitic}$ from the $\theta_{Control}$.

Such a setting can be implemented at the sensor level as follows:

When a surgeon initially starts working with the device, the handle's absolute yaw, pitch and roll $\{y, p, r\}$ are initialized and set to correspond to a straight articulation $\{y_0, p_0, r_0\}$. The articulation bending is controlled by the handle's shifted orientation:

$$\begin{bmatrix} y_i \\ p_i \\ r_i \end{bmatrix} = \begin{bmatrix} y \\ p \\ r \end{bmatrix} - \begin{bmatrix} y_0 \\ p_0 \\ r_0 \end{bmatrix}$$

User can initialize $\{y_0, p_0, r_0\}$ at any point.

Figure 17:
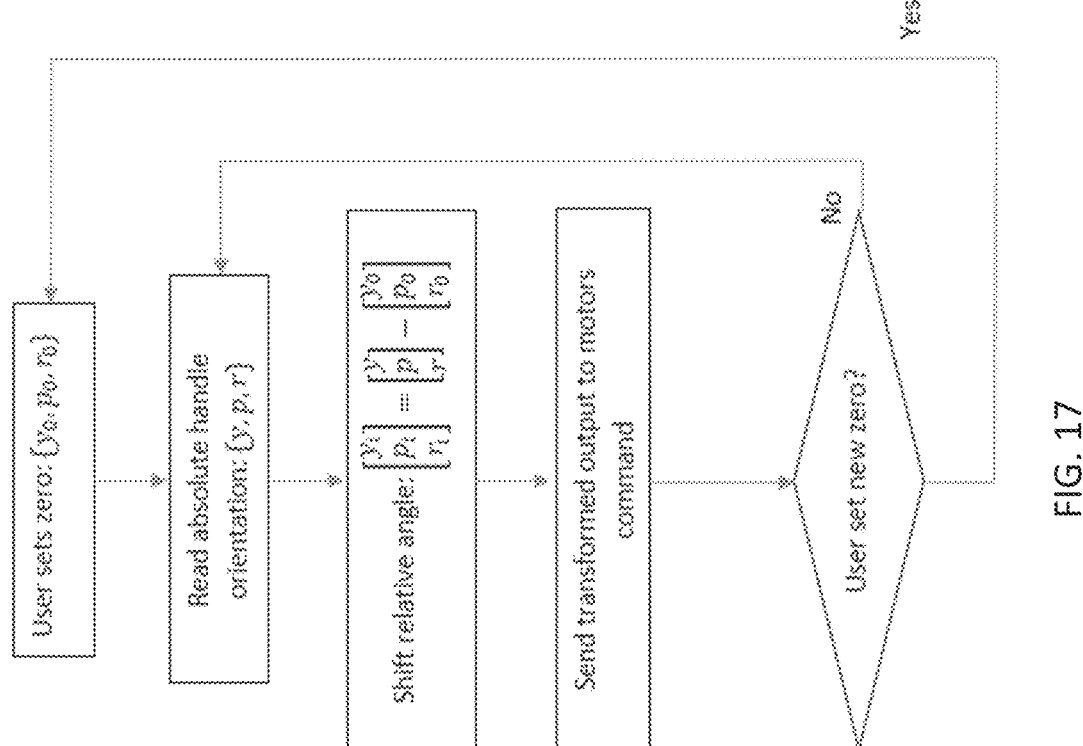

FIG. 17 is a flowchart diagram describing this process.

Alternatively in an embodiment using a single IMU sensor, when user initially starts working with the device, the device's absolute yaw, pitch and roll $\{y_{d_n}, p_{d_n}, r_{d_n}\}$ are initialized $\{y_{d_n}, p_{d_n}, r_{d_n}\}$.

Let the relative yaw, pitch and roll angles between the handle and the device be $\{y_h, p_h, r_h\}$. The articulation bending is controlled by the handle's shifted orientation:

$$\begin{bmatrix} y_i \\ p_i \\ r_i \end{bmatrix} = \begin{bmatrix} y_h \\ p_h \\ r_h \end{bmatrix} - \left( \begin{bmatrix} y_d \\ p_d \\ r_d \end{bmatrix} - \begin{bmatrix} y_{d_0} \\ p_{d_0} \\ r_{d_0} \end{bmatrix} \right)$$

User can initialize $\{y_{d_n}, p_{d_n}, r_{d_n}\}$ at any point.

Figure 18:
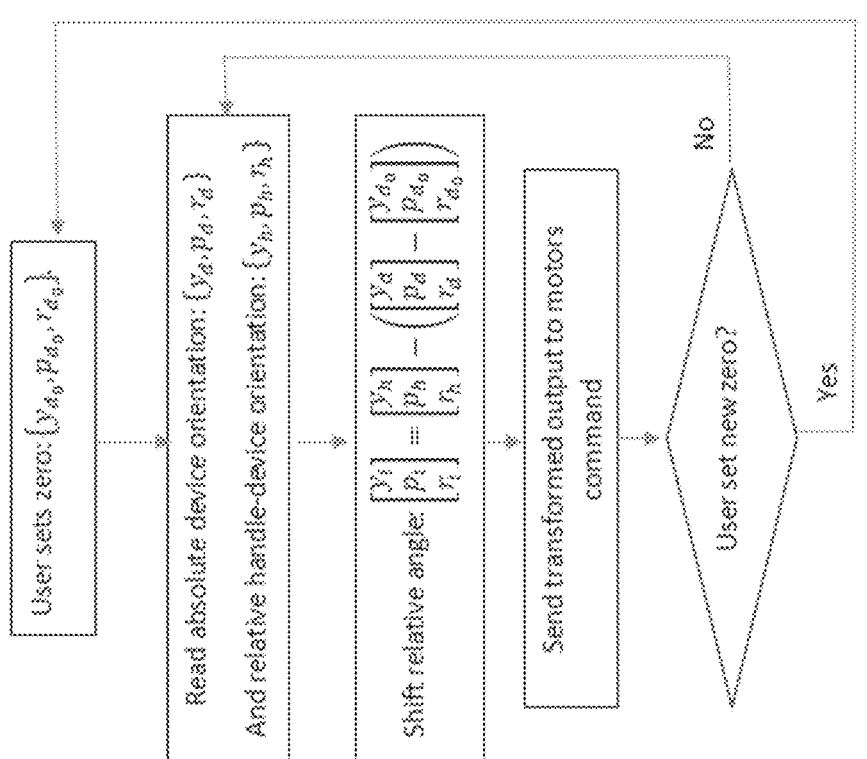

FIG. 18 is a flowchart diagram describing this process.

Implementation of a Lock Orientation Mode

Lock orientation mode allows the user to keep the tip absolute orientation (with respect to the inertial coordinate system). The ability to keep the tip absolute orientation when changing the device's orientation is useful when for example, the surgeon preforms number of sutures along a suture line.

Such a setting can be implemented at the sensor level as follows:

When a user enters lock orientation mode, the device's absolute yaw, pitch and roll $\{y_d, p_d, r_d\}$ are initialized $\{y_{d_n}, p_{d_n}, r_{d_n}\}$. Also, the tip's relative angle to device $\{y_t, p_t, r_t\}$ is initialized $\{y_{t_n}, p_{t_n}, r_{t_n}\}$. The articulation bending movement compensates for the device movement and keeps the tip in the same absolute orientation:

$$\begin{bmatrix} y_i \\ p_i \\ r_i \end{bmatrix} = \begin{bmatrix} y_{t_0} \\ p_{t_0} \\ r_{t_0} \end{bmatrix} - \left( \begin{bmatrix} y_d \\ p_d \\ r_d \end{bmatrix} - \begin{bmatrix} y_{d_0} \\ p_{d_0} \\ r_{d_0} \end{bmatrix} \right)$$

During lock orientation mode, handle orientation does not control the bending of the articulation while keeping the ability to control the jaws. When user exits the mode, a clutch function, similar to the "handle-articulation ergonomics settings mode" described above, can correlate between current articulation and device handle and arm orientation to continue working from that point (depending on chosen control function).

Figure 19:
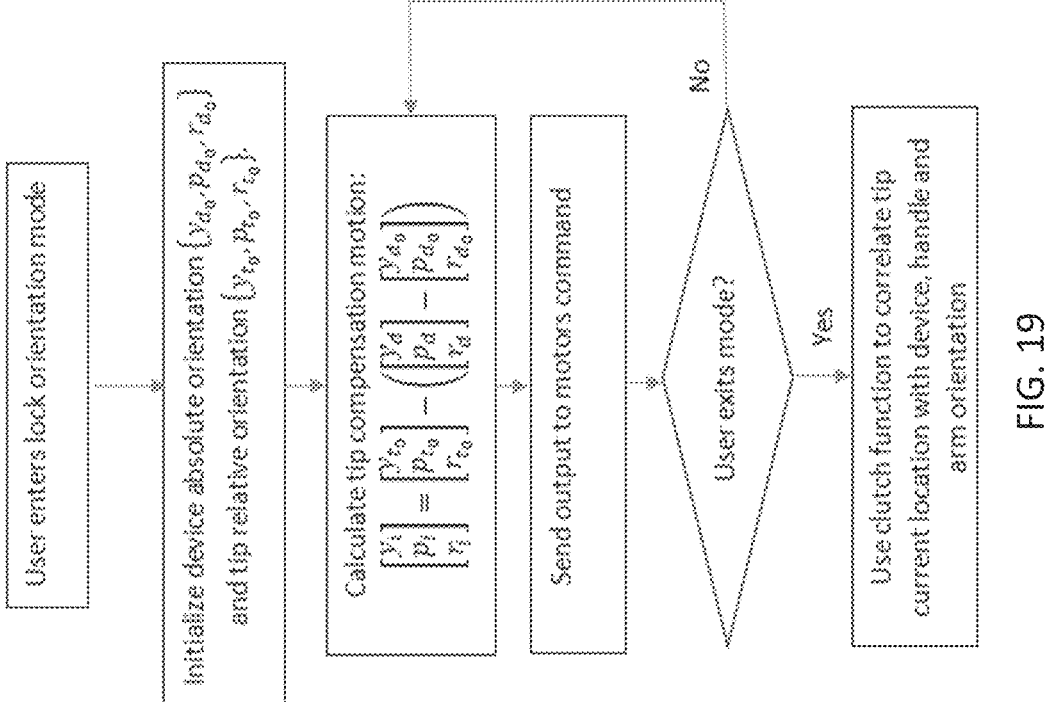

FIG. 19 is a flowchart description of this function.

Implementation of Wrist Control Mode

The "wrist control mode" aims to avoid parasitic motion caused by the relative movement between the handle and device, by measuring the relative angle between a user's arm and the control interface handle. This control mode allows the user to control the tip orientation more instinctively by envisioning the wrist angles as directly controlling the tip.

Such a setting can be implemented at the sensor level as follows. When a user initially starts working with the device in wrist control mode, the relative yaw and pitch $\{y,p\}$ of the handle and arm are initialized and set to correspond to a straight articulation orientation $\{y_0, p_0\}$. Articulation bending movement is controlled by a shifted orientation of the handle:

$$\begin{bmatrix} y_i \\ p_i \end{bmatrix} = \begin{bmatrix} y \\ p \end{bmatrix} - \begin{bmatrix} y_0 \\ p_0 \end{bmatrix}.$$

The user can initialize $\{y_0, p_0\}$ at any point.

Figure 20:
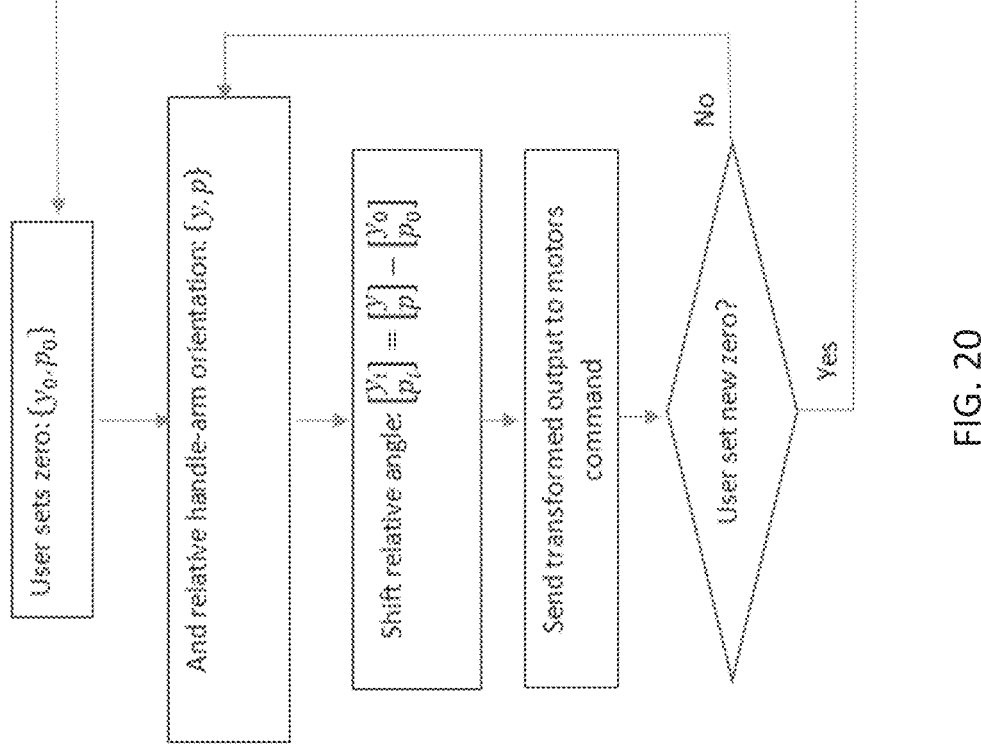

FIG. 20 is a flowchart description of this function.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. In addition, any priority document(s) of this application is/are hereby incorporated by reference in its/their entirety.

What is claimed is:

1. A controller for a surgical tool comprising a user interface having a housing with finger pad levers mounted thereupon said housing including a recess having an openable cover for storing a removable sensor pack including a capsule sealingly encapsulating a plurality of sensors, said plurality of sensors being isolated from internal components of said housing and an external environment by said capsule, said sensor pack being for determining a spatial orientation of said housing of said user interface, a rotational orientation of said finger pad levers and an angle between said fingers pad levers and for wirelessly transmitting data obtained by said sensors to at least one motor to control operation of the surgical tool.

2. The controller of claim 1, wherein said housing includes an additional sensor for calibrating an orientation signal of said sensor pack.

5

\*　\*　\*　\*　\*